(12) United States Patent
Fujita et al.

(10) Patent No.: US 9,001,321 B2
(45) Date of Patent: Apr. 7, 2015

(54) MICROSCOPE AND OBSERVATION METHOD

(75) Inventors: Katsumasa Fujita, Osaka (JP); Shogo Kawano, Osaka (JP); Masahito Yamanaka, Osaka (JP); Satoshi Kawata, Osaka (JP)

(73) Assignee: Osaka University, Osaka (JP)

( * ) Notice: Subject to any disclaimer, the term of this patent is extended or adjusted under 35 U.S.C. 154(b) by 267 days.

(21) Appl. No.: 13/578,164

(22) PCT Filed: Feb. 8, 2011

(86) PCT No.: PCT/JP2011/000697
§ 371 (c)(1),
(2), (4) Date: Aug. 9, 2012

(87) PCT Pub. No.: WO2011/099269
PCT Pub. Date: Aug. 18, 2011

(65) Prior Publication Data
US 2012/0307238 A1    Dec. 6, 2012

(30) Foreign Application Priority Data

Feb. 10, 2010   (JP) ................................. 2010-027838

(51) Int. Cl.
*G01J 3/44*        (2006.01)
*G02B 21/00*    (2006.01)
*G01N 21/65*    (2006.01)

(52) U.S. Cl.
CPC ........ *G02B 21/002* (2013.01); *G01N 2021/653* (2013.01); *G01N 2021/655* (2013.01); *G02B 2207/114* (2013.01)

(58) Field of Classification Search
USPC ............................................. 356/301, 72–73
See application file for complete search history.

(56) References Cited

U.S. PATENT DOCUMENTS 8,027,032 B2 *   9/2011   Xie et al. ..................... 356/301

FOREIGN PATENT DOCUMENTS

JP           2007-192742 A     8/2007
WO         2006-061947 A1    6/2006

* cited by examiner

*Primary Examiner* — Abdullahi Nur
(74) *Attorney, Agent, or Firm* — Maier & Maier, PLLC

(57) ABSTRACT

Provided is a microscope and an observation method which can improve spatial resolution. A microscope according to an aspect of the invention includes a laser light source (10), an objective lens (16) that focuses light from the laser light source on a sample, and a detector (22) that detects the laser light as signal light from a sample (17) when the sample (17) is irradiated with the laser light. The light is applied to the sample with an intensity changed to obtain a nonlinear region where intensities of the light and the signal light have a nonlinear relation due to occurrence of saturation or nonlinear increase of the signal light when the light has a maximum intensity, and the detector (22) detects the signal light according to the intensity of the laser light to perform observation based on a saturation component or a nonlinear increase component of the signal light.

20 Claims, 17 Drawing Sheets

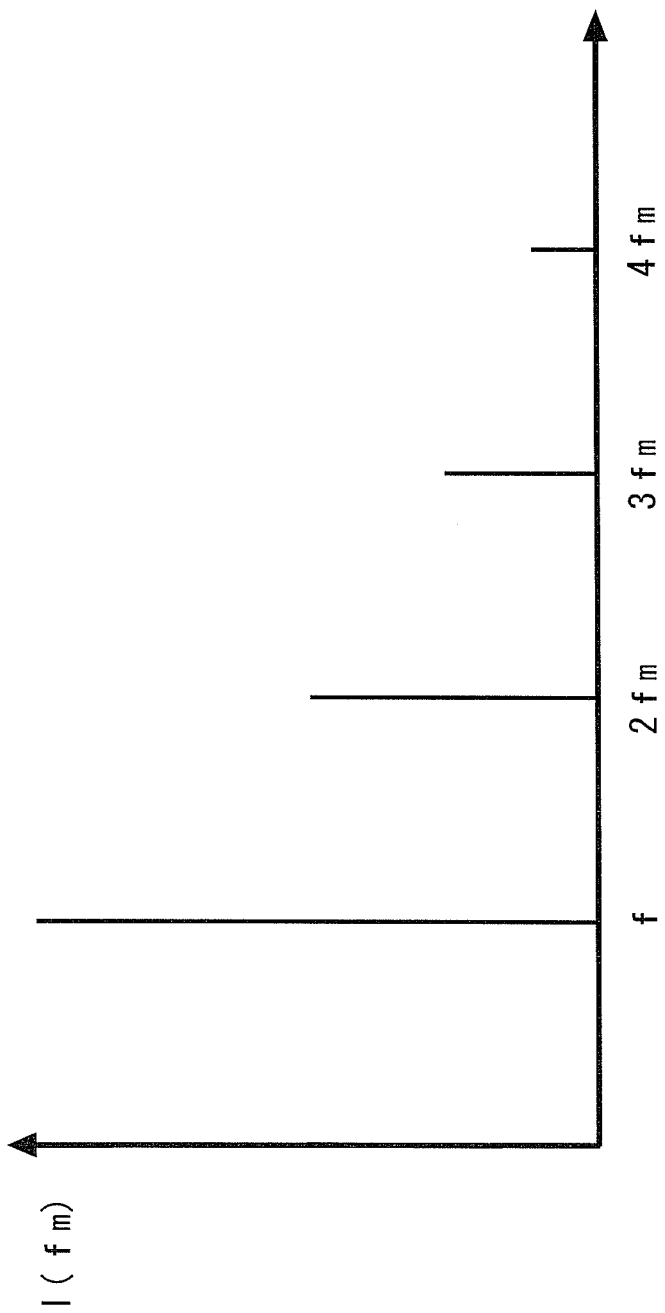

MICROSCOPE AND OBSERVATION METHOD

TECHNICAL FIELD

The present invention relates to a microscope and an observation method.

BACKGROUND ART

A spatial resolution of a general microscope is limited by diffraction limit. Thus, existing microscopes have a problem that once a light wavelength and a numeric aperture are determined, the spatial resolution cannot be increased beyond a certain level.

The inventors of this application have proposed a fluorescence microscope to improve the spatial resolution (Patent Literature 1). In this fluorescence microscope, observation is performed based on saturation components of fluorescence.

CITATION LIST

Patent Literature

[Patent Literature 1] International Patent Publication No. WO2006/061947

SUMMARY OF INVENTION

Technical Problem

However, the fluorescence microscope described above has a problem that the spatial resolution for components other than fluorescence cannot be improved.

The present invention has been accomplished in view of the above-mentioned problem, and an object of the invention is to provide a microscope and an observation method which can improve spatial resolution.

Solution to Problem

A microscope according to a first aspect of the present invention includes: at least one light source that emits light; a lens that focuses light emitted from the light source and irradiates a sample with the light; and at least one detector that detects signal light generated by a multi-photon transition process in the sample when the sample is irradiated with the light. The light is applied to the sample with an intensity changed to obtain a nonlinear region in which an intensity of the light and an intensity of the signal light have a nonlinear relation due to occurrence of saturation or nonlinear increase generated by a non-linear optical effect when the light has a maximum intensity, and the detector detects the signal light according to the intensity of the light to perform observation based on one of a saturation component and a nonlinear increase component of the signal light. This enables observation based on one of saturation and nonlinear increase of the signal light due to a nonlinear optical loss.

According to a second aspect of the present invention, in the microscope, the detector detects, as the signal light, at least one of reflection light, transmitted light, and scattered light having the same wavelength as that of the light from the light source, and generation of optical harmonics due to other optical effects including a higher-order nonlinear optical effect causes the signal light to be saturated.

According to a third aspect of the present invention, in the microscope, the detector detects, as the signal light, scattered light generated by a multi-photon transition, and generation of optical harmonics due to other optical effects including the nonlinear optical effect causes the signal light to be saturated.

According to a fourth aspect of the present invention, in the microscope, the detector detects at least one of hyper-Rayleigh scattering, Raman scattering, stimulated Raman scattering, coherent anti-Stokes Raman scattering, four wave mixing, stimulated emission, harmonics generation, difference frequency generation, and sum frequency generation, and signal light detected by the detector is separated from the light by using a wavelength difference from the light emitted from the light source. This enables observation with a high resolution using various types of light.

According to a fifth aspect of the present invention, the microscope further includes a modulator that performs intensity modulation such that the intensity of the light changes according to time. In the microscope, the light is applied to the sample with an intensity where the signal light has the nonlinear region at a peak time of the light; the modulator performs intensity modulation and scans relative positions of the light and the sample such that the relative positions are changed, and the detector detects the signal light emitted from the sample; and a harmonic component for a modulation frequency in the modulator is extracted from the signal light detected by the detector and is observed. This enables generation of one of saturation and nonlinear increase due to a nonlinear optical loss with simplicity.

According to a sixth aspect of the present invention, in the microscope, the signal light emitted from the sample is generated by an n-photon reaction (n is a natural number of 1 or more) of light, the intensity of the light being modulated by the modulator, and a (n+1) or higher-order harmonic component for the modulation frequency in the modulator is extracted and observed. This enables generation of one of saturation and nonlinear increase without increasing the intensity of the light incident on the sample in a one-photon reaction and a multi-photon reaction.

According to a seventh aspect of the present invention, in the microscope, the sample is irradiated with two light beams having different wavelengths; the two light beams are intensity-modulated with the same modulation frequency and the same phase; the signal light emitted from the sample is generated by an m-photon reaction (m is a natural number of 2 or more) of the two light beams modulated by the modulator; and a (m+1) or higher-order harmonic component for the modulation frequency is extracted and observed. This enables generation of one of saturation and nonlinear increase in a multi-photon reaction without increasing the intensity of the light incident on the sample.

According to an eighth aspect of the present invention, in the microscope, the sample is irradiated with two light beams having different wavelengths; the two light beams are modulated with different modulation frequencies; and the light beams are demodulated with a frequency corresponding to one of a sum and a difference between the modulation frequencies.

According to a ninth aspect of the present invention, in the microscope, intensity modulation is performed such that the intensity of the light changes according to time; the light source is a pulse light source; and a repetition frequency of the pulse light source is higher than the modulation frequency for the intensity modulation.

According to a tenth aspect of the present invention, in the microscope, the intensity of the light is changed such that the signal light is applied to the sample with at least two intensities of a first intensity corresponding to the nonlinear region and a second intensity different from the first intensity; and one of a saturation component and a nonlinear increase component of the signal light is calculated based on the intensity of the signal light at the first intensity and the intensity of the signal at the second intensity. This enables observation based on one of a saturation component and a nonlinear increase component with a simple configuration.

According to an eleventh aspect of the present invention, in the microscope, the signal light separated according to a wavelength difference is detected by a plurality of the detectors.

An observation method according to a twelfth aspect of the present invention irradiates a sample with light and observes the sample, the method including: focusing the light and irradiating the sample with the light to generate signal light by a multi-photon transition process in the sample; changing an intensity of the light to obtain a nonlinear region in which an intensity of the light and an intensity of the signal light have a nonlinear relation due to occurrence of saturation or nonlinear increase generated by a non-linear optical effect when the light has a maximum intensity; detecting the signal light from the sample; and performing observation based on one of a saturation component and a nonlinear increase component of the signal light detected. This enables observation based on one of saturation of and nonlinear increase of the signal light due to a nonlinear optical loss, thereby enabling observation with a high spatial resolution without detecting harmonic generation.

According to a thirteenth aspect of the present invention, in the observation method, the sample is irradiated with the light in a state where a metallic probe is disposed near the sample or in a state where metal particles are added to the sample. This enables observation based on generation of one of saturation and nonlinear increase due to a nonlinear optical loss and based on one of the saturation and the nonlinear increase, with simplicity.

According to a fourteenth aspect of the present invention, in the observation method, the signal light is detected by scanning the metallic probe disposed near the sample and irradiating the sample with the light. This enables observation based on generation of one of saturation and nonlinear increase due to a nonlinear optical loss and based on one of the saturation and the nonlinear increase, with simplicity.

Advantageous Effects of Invention

According to the present invention, it is possible to provide a microscope and an observation method which can improve a spatial resolution.

BRIEF DESCRIPTION OF DRAWINGS

FIG. 5 is a graph schematically showing a power spectrum of reflection light intensity with respect to frequency;

DESCRIPTION OF EMBODIMENTS

Hereinafter, specific embodiments to which the present invention is applied will be described in detail with reference to the drawings. However, the present invention is not limited to the embodiments described below. The following description and the drawings are simplified as appropriate for clarity of explanation.

First Embodiment

Figure 1:
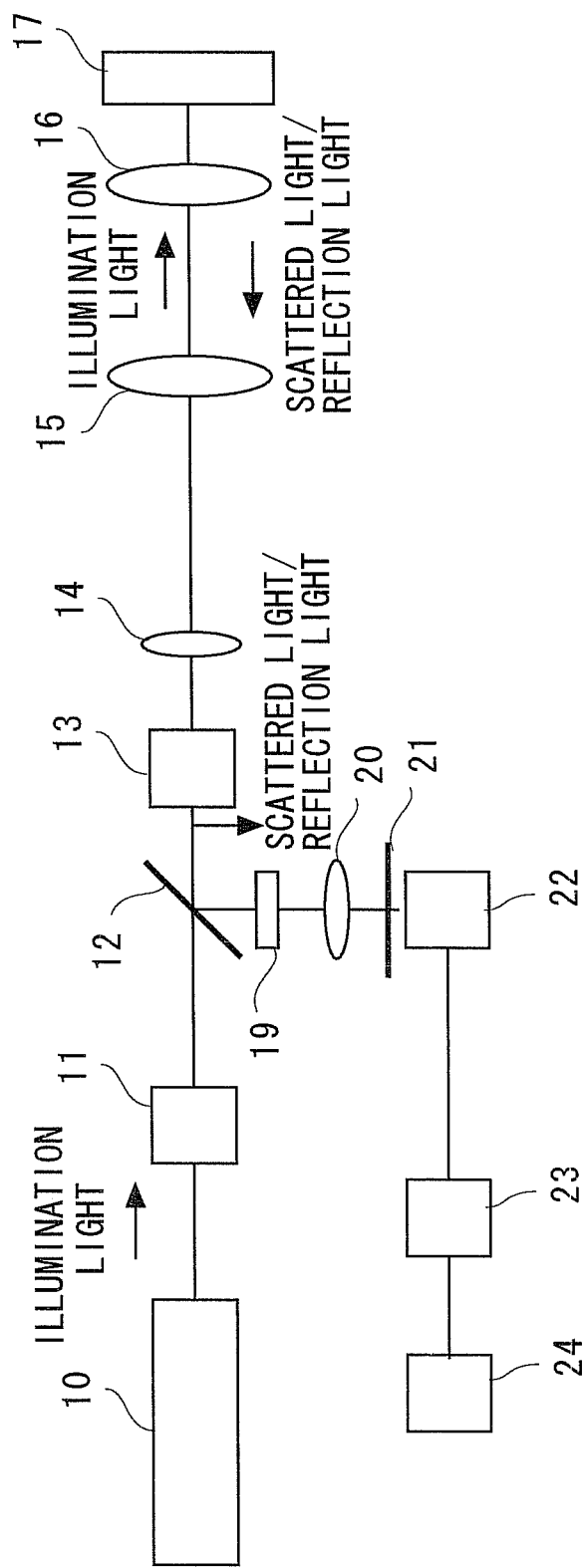
FIG. 1 is a diagram showing a configuration of a laser microscope according to an embodiment of the present invention.

In this embodiment, a spatial resolution is improved by utilizing saturation of reflection light, scattered light, or transmitted light. That is, an observation of saturation components of reflection light, transmitted light, or scattered light improves a spatial resolution. A laser microscope according to a first embodiment of the present invention is a confocal microscope, in other words, a laser scanning type microscope. This laser microscope is described with reference to FIG. 1. FIG. 1 is a diagram schematically showing the configuration of the laser microscope according to the present invention. Reference numeral 10 denotes a light source; 11, a modulator; 12, a beam splitter; 13, a scanner; 14, a lens; 15, a lens; 16, an objective lens; 19, a filter; 20, a lens; 21, a pinhole; 22, a detector; 23, a lock-in amplifier; and 24, a processing apparatus. The laser microscope shown in FIG. 1 detects reflection light (or scattered light).

The light source 10 is a laser light source that continuously emits illumination light; for example, a continuous-wave Ar ion laser or a semiconductor laser having a wavelength in a visible range can be used. Here, the laser wavelength is represented by $\lambda$. Laser light serving as illumination light is intensity-modulated with the modulator 11, and takes a periodic function with a frequency $f_m$. In this example, intensity modulation is performed such that the intensity of the laser light takes a cosine function. Assuming that $f_m$ represents a frequency in intensity modulation; $\omega_m (=2\pi f_m)$ represents an angular frequency; and t represents time, the laser light intensity is proportional to $1+\cos(\omega_m t)$. The intensity of the intensity-modulated laser light takes a maximum value at $\omega_m t = 2n\pi$ and a minimum value at $\omega_m t=(2n+1)\pi$ (n is an arbitrary natural number). Note that an initial phase is 0. In this example, light is modulated with $f_m$=100 kHz, for example. As the modulator 11, an electro-optical modulator, an acousto-optical modulator, or the like may be used.

The intensity-modulated laser light enters the beam splitter 12. The beam splitter 12 reflects a half of the incident light and transmits the remaining half of the light. The laser light transmitted through the beam splitter 12 enters the scanner 13. The scanner 13 scans the laser light and changes the propagation direction of the laser light, thereby changing the position of the laser light on a sample 17. Note that the scanner 13 is used in the above description, but a driving stage or the like may also be used instead of the scanner 13. Instead of scanning with laser light, the stage or the like on which the sample 17 is placed may be driven. A combination thereof may also be used, as a matter of course. For example, the scanner 13 may perform scanning in an X-direction and the stage may perform scanning in a Y-direction. That is, any configuration may be employed as long as scanning is performed while changing a relative position between laser light and the sample 17. Note that the scanning is not limited to scanning only in two-dimensional directions. Scanning in three dimensions may also be used.

The laser light scanned by the scanner 13 passes through the lens 14 and the lens 15. The light refracted by the lenses 14 and 15 enters the objective lens 16. The objective lens 16 focuses the laser light onto the sample 17 or into the sample 17. When the laser light serving as illumination light enters the sample 17, the illumination light is scattered or reflected. Accordingly, one or both of scattered light and reflection light exit from the sample 17. Hereinafter, the light emitted from the sample 17 according to laser light is referred to as "scattered light/reflection light".

The scattered light/reflection light emitted from the sample 17 enters the objective lens 16. The scattered light/reflection light is refracted by the objective lens 16 and enters the lens 15 and the lens 14. The scattered light/reflection light refracted by the lenses 15 and 14 is descanned by the scanner 13. Then, the scattered light/reflection light descanned by the scanner 13 is reflected by the beam splitter 12 and enters the filter 19.

The filter 19 is an optical filter, for example, and splits the light according to the wavelength. The filter 19 transmits the wavelength of laser light and blocks optical harmonics. That is, the filter 19 extracts only fundamental waves from the scattered light/reflection light emitted from the sample 17. Accordingly, the second or higher-order harmonics are blocked by the filter 19.

The scattered light/reflection light transmitted through the filter 19 passes through the lens 20. The lens 20 enters the pinhole 21. The pinhole 21 has a light transmission hole formed at the center thereof to allow the scattered light/reflection light to pass therethrough. That is, the light transmission hole of the pinhole 21 is disposed on the optical axis. The objective lens 16, the lens 15, the lens 14, and the lens 20 are arranged so that an image formed on the sample 17 is focused on the pinhole 21. The scattered light/reflection light having passed through the pinhole 21 enters the detector 22. The detector 22 measures the intensity of the received scattered light/reflection light.

The scattered light/reflection light entering the detector 22 is based on the intensity-modulated laser light. The detector 22 is a sensor such as a photoelectron multiplier. This detector 22 outputs a detection signal to the lock-in amplifier 23 in accordance with the intensity of the received light. The lock-in amplifier 23 locks in a predetermined repetition frequency, and lock-in detects a signal from the detector 22. Here, the lock-in amplifier 23 receives a reference signal from the modulator 11, and demodulates the signal with a frequency n times (n is an integer of 2 or more) higher than a modulation frequency $f_m$ of the modulator 11. For example, assuming that the modulation frequency $f_m$ is 100 kHz, the signal is demodulated with a frequency of 200 kHz, 300 kHz, . . . . As a result, high-order modulation frequency components can be extracted and detected.

Further, the processing apparatus 24 controls the scanner 13, the modulator 11, and the lock-in amplifier 23 to perform lock-in detection during the scanning operation of the sample 17. In addition, the processing apparatus 24 forms an optical image based on the signal output from the lock-in amplifier 23. In other words, an optical image is formed based on the detected signal during the scanning operation of the sample 17. The optical image can be displayed on a screen or data on the optical image can be stored by the processing apparatus 24 executing predetermined operations. As a result, the optical image can be observed or captured by scattered light or reflection light.

The laser microscope according to this embodiment configures a confocal microscope. That is, the components are arranged such that the laser light source 10 serving as a point light source is in optically conjugate relationship with the sample 17, and the sample 17 is in optically conjugate relationship with the pinhole 21. This enables detection of the scattered light/reflection light through a confocal optical system. Hence, the spatial resolution can be improved.

Figure 2:
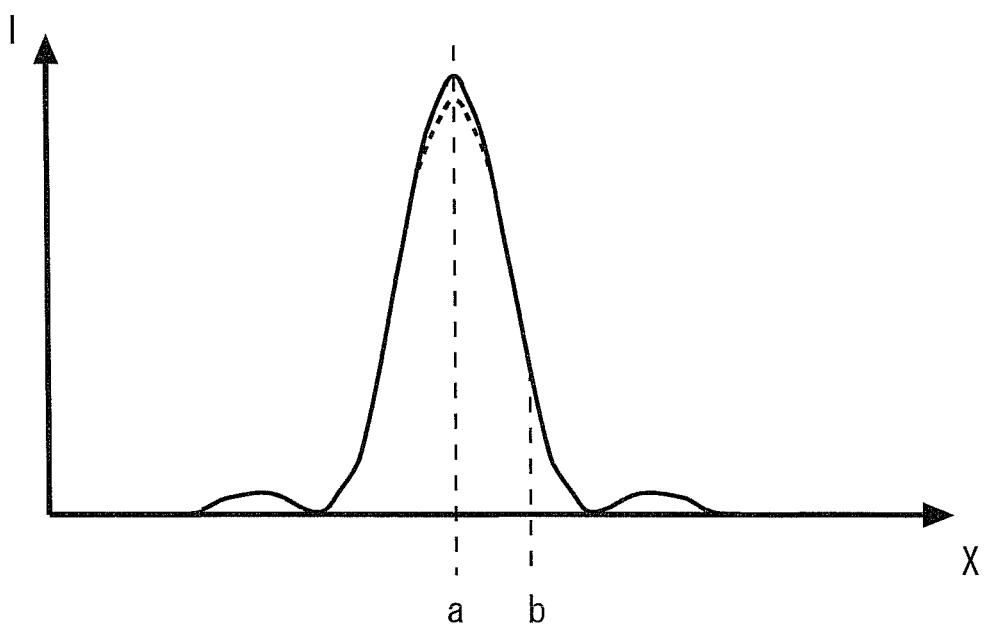
FIG. 2 is a graph schematically showing a spatial distribution of scattered light and reflection light.
Figure 3A:
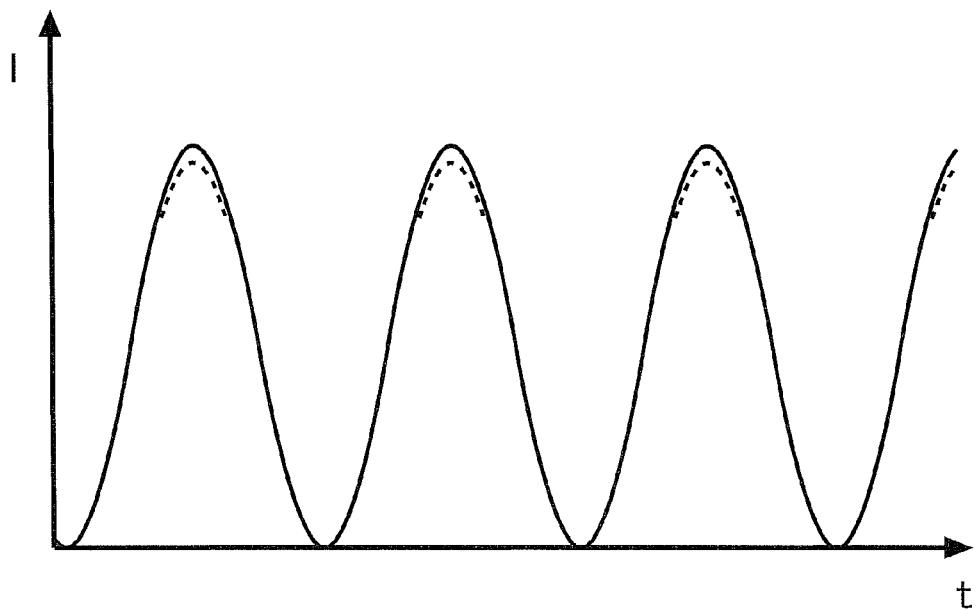
FIG. 3A is a graph schematically showing a change in intensity of modulated laser light and scattered light generated by irradiation of laser light.
Figure 3B:
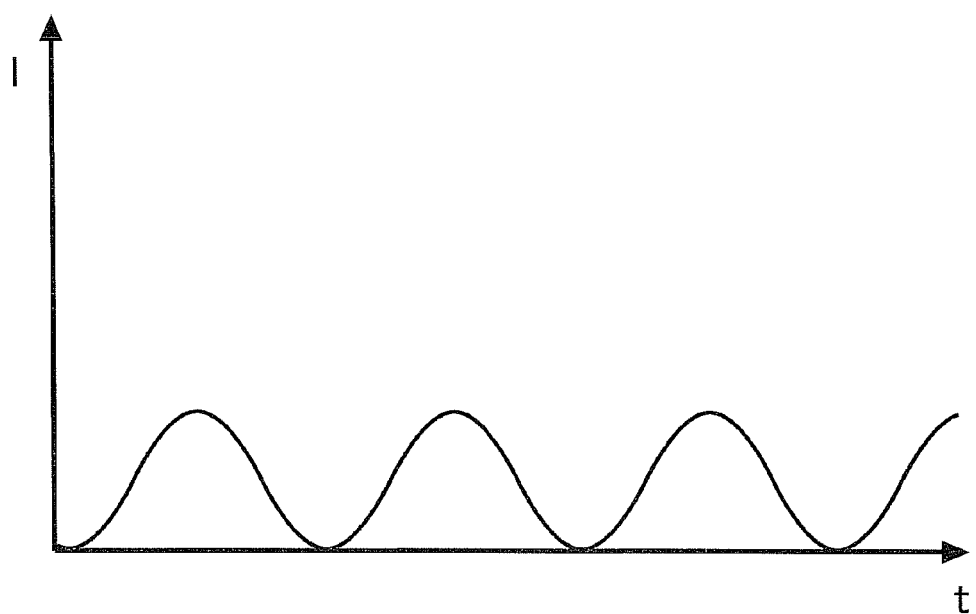
FIG. 3B is a graph schematically showing a change in intensity of modulated laser light and scattered light generated by irradiation of laser light.
Figure 4:
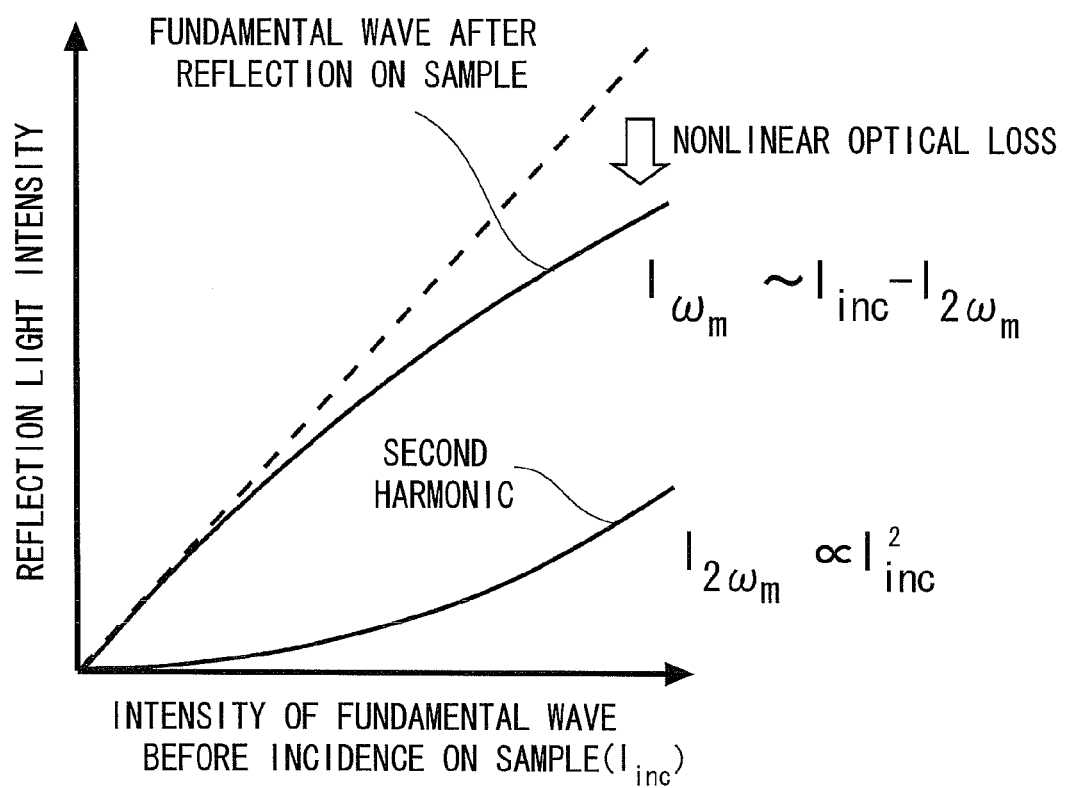
FIG. 4 is a graph schematically showing a relation between the intensity of reflection light and the intensity of harmonics with respect to laser light intensity.

Next, the principle of high-resolution detection utilizing saturation of light will be described with reference to FIGS. 2 to 4. In the following description, an example of detecting reflection light will be described. FIG. 2 is a graph showing a spatial distribution of intensities of laser light and reflection light. In FIG. 2, the horizontal axis represents a position, and the vertical axis represents light intensity. FIGS. 3A and 3B are graphs each showing a change with time in intensity of intensity-modulated laser light and reflection light. In FIGS. 3A and 3B, the horizontal axis represents time, and the vertical axis represents light intensity. Further, in FIG. 2 and FIGS. 3A and 3B, the solid line represents laser light intensity, and the dashed line represents reflection light intensity. For clarity of explanation, in FIG. 2 and FIGS. 3A and 3B, the intensity of the reflection light corresponds to the intensity of the laser light intensity when the reflection light is not saturated. FIG. 4 is a graph showing a relation between the laser light intensity and the intensity of the light emitted from the sample. In FIG. 4, the horizontal axis represents laser light intensity, and the vertical axis represents signal light intensity.

As shown in FIG. 2, the intensity of laser light reaches its peak at the center of a spot (a position represented by x=a) and decreases with distance from the spot center. In this embodiment, the laser light intensity is modulated. Accordingly, the laser light intensity changes with time at x=a as shown in FIG. 3A, and the laser light intensity changes with time at x=b as shown in FIG. 3B. That is, since the intensity of the laser light is modulated, the laser light changes in any position in accordance with a cosine function. Here, x=a represents a peak position, and x=b represents an off-peak position. Thus, the laser light intensity at x=a is higher than the laser light intensity at x=b at any timing.

If the laser light intensity increases, the reflection light is saturated. When the laser light intensity is extremely high, for example, optical harmonics of the laser light are generated by a nonlinear optical effect. That is, light having a wavelength that is an integral multiple of a laser wavelength is generated. The original laser light intensity is reduced by the amount of generated optical harmonics, and a harmonic loss occurs. Note that the term "harmonic loss" refers to a phenomenon in which the intensity of signal light such as scattered light, transmitted light, or reflection light from a sample is lost and saturated due to a higher-order nonlinear optical effect or other optical effects. Accordingly, this harmonic loss can be referred to as a nonlinear optical loss (hereinafter referred to as a nonlinear optical loss). That is, the intensity of the reflection light is reduced by the amount of the generated nonlinear optical loss. Hereinafter, the optical harmonics of laser light generated in the sample are defined as laser harmonics. Assuming that $\lambda$ represents a laser wavelength serving as a fundamental wave, the wavelength of the laser harmonics is represented by $n\lambda$ (n is a natural number of 2 or more). In the following description, the optical harmonics of the reflection light may be defined as laser harmonics. Further, in the following description, reflection light having the same wavelength as that of laser light is illustrated.

When the intensity of the laser light is low as shown in FIG. 4, the laser light and the reflection light are proportional to each other. However, as the intensity of the laser light increases, the laser light and the reflection light are not proportional to each other. Thus, even when the intensity of the laser light is increased, the obtained reflection light is saturated instead of increasing in proportion. That is, if there is no saturation due to the nonlinear optical loss, the reflection light intensity increases in proportion to the laser light intensity as indicated by the dashed line of FIG. 4. In practice, however, saturation occurs from a certain laser light intensity as indicated by the solid line, and the reflection light intensity hits a peak. Note herein that the phrase "saturation due to a nonlinear optical loss" refers to a phenomenon in which the relation between the laser light intensity and the reflection light intensity deviates from the linear relation. That is, referring to FIG. 4, at the reflection light intensity where the dashed line and the solid line are spaced apart from each other, saturation of reflection light components occurs. In other words, a saturation region in which saturation of the reflection light occurs is a nonlinear region in which the reflection light intensity has a nonlinear relation with the laser light intensity. In the nonlinear region, the reflection light having the same wavelength as the laser wavelength is reduced by the amount of optical harmonics of the reflection light.

Such saturation of the reflection light is more likely to occur as the laser intensity increases. Further, as the laser intensity increases, the saturation degree increases. Accordingly, the laser light having the spatial distribution shown in FIG. 2 is more likely to be saturated toward the peak position (x=a), and the saturation degree of the reflection light is greatest at the peak position. Further, the laser light that is intensity-modulated to each cosine function as shown in FIGS. 3A and 3B is more likely to be saturated during a time ($\omega_m t=2n\pi$) corresponding to the vicinity of each peak, and the saturation degree of the reflection light is greatest during the time corresponding to the peak.

Assume herein that in the portion represented by x=b, the reflection light is not saturated at any time and the laser light having such an intensity that causes the reflection light to be saturated in the vicinity of the peak position (x=a) is applied to the sample 17. As a result, the reflection light having the intensity distribution as indicated by the dashed line shown in FIG. 2 is emitted. Specifically, referring to FIG. 2, in the vicinity of the peak position (x=a), a difference in intensity occurs between the laser light and the reflection light, and the waveforms of the laser light and the reflection light substantially match each other with distance from the peak position.

Further, the reflection light has an intensity as indicated by the dashed line of FIG. 3A with respect to the intensity-modulated laser light. That is, the intensity of the laser light is high in the portion represented by x=a, so that the reflection light is saturated. As shown in FIG. 3A, saturation of the reflection light occurs at about the time ($\omega_m t=2n\pi$) corresponding to each peak, but does not occur at about the time ($\omega_m t=(2n+1)\pi$) between peaks. That is, in FIG. 3A, a difference in intensity between the laser light and the reflection light occurs at about the time corresponding to each peak, and the laser light and the reflection light match each other after the time corresponding to each peak. On the other hand, the intensity of the laser light is low in the portion represented by x=b, so that the reflection light is not saturated at any time. Accordingly, the laser light intensity and the reflection light intensity are proportional to each other. FIG. 3B shows that these intensities match each other.

In the portion represented by x=b, the reflection light intensity is proportional to $1+\cos(\omega_m t)$. On the other hand, in the portion represented by x=a, the intensity of the reflection light decreases at about the time corresponding to each peak due to the saturation of the reflection light, so that the reflection light intensity is not proportional to $1+\cos(\omega_m t)$. That is, in the portion represented by x=a, second-order, third-order, . . . harmonic components (harmonics with respect to the intensity modulation by the modulator 11) appear in the reflection light intensity. The detection of these harmonics enables extraction of information on only the spot center of the laser light. That is, the harmonic components of the intensity modulation include information on the spot center of the laser light.

The intensity of the reflection light obtained when no saturation occurs is proportional to the reflectance and the incident light intensity. The intensity of the laser light is expressed as $B \cdot (1+\cos(\omega_m t))$ and is proportional to $(1+\cos(\omega_m t))$. Note that "B" represents an amplitude. When saturation occurs, the reflection light intensity is represented by a function of $(1+\cos(\omega_m t))$. Accordingly, when the reflection light intensity is subjected to Taylor expansion, the intensity can be expressed as power series of $(1+\cos(\omega_m t))$. That is, the term of the n-th power of $(1+\cos(\omega_m t))$ appears. Then, the term $\cos(2\omega_m t)$ appears in $(1+\cos(\omega_m t))^2$ and the term $\cos(3\omega_m t)$ appears in $(1+\cos(\omega_m t))^3$. Thus, modulation harmonic components appear. Note that the term "modulation harmonics" refers to harmonics with respect to the intensity modulation of the laser light intensity by the modulator 11, and are used to be distinguished from optical harmonics of laser light, i.e., light having a wavelength $\lambda/n$.

Here, when a spectrum for a modulation frequency is obtained by performing Fourier transform on the reflection light intensity indicated by the dashed line of FIG. 3A, an amplitude spectrum as shown in FIG. 5 is obtained. FIG. 5 is a diagram schematically showing the amplitude spectrum with respect to the modulation frequency. Since the reflection light is represented by a periodic function, the spectrum thereof is a line spectrum having a peak at a predetermined frequency.

As described above, the modulation harmonic components appear in the reflection light, so that peaks appear at positions of $f_m$, $2f_m$, $3f_m$, $4f_m$, . . . . Assuming herein that the laser light has an amplitude B, the height of the peak at a position $nf_m$ is proportional to $B^n$. For example, the peak at the position $f_m$ is proportional to B, and the peak at the position $2f_m$ is proportional to $B^2$.

Figure 6A:
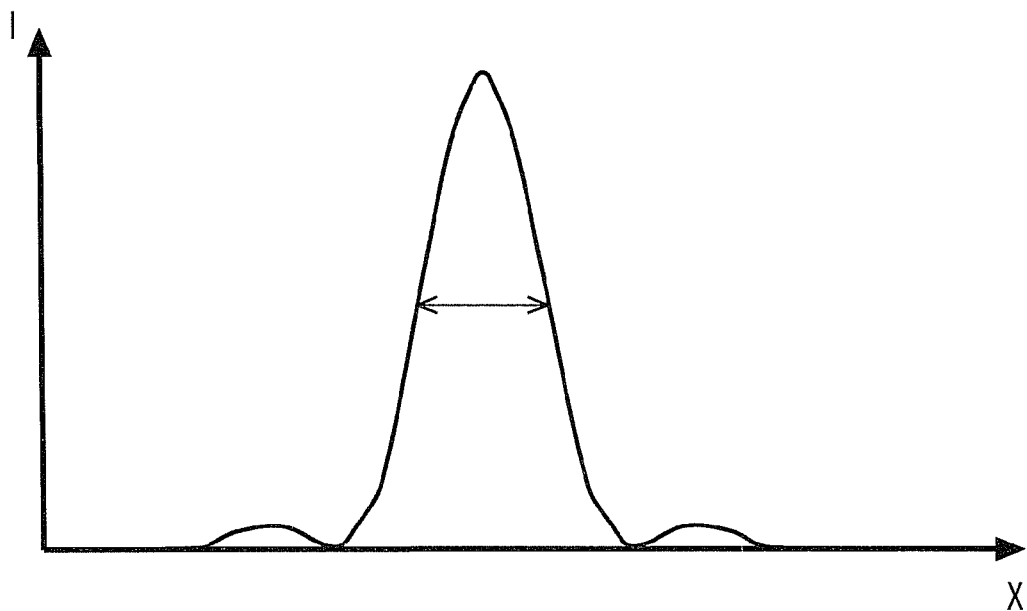
FIG. 6A is a graph schematically showing a spatial distribution of reflection light.
Figure 6B:
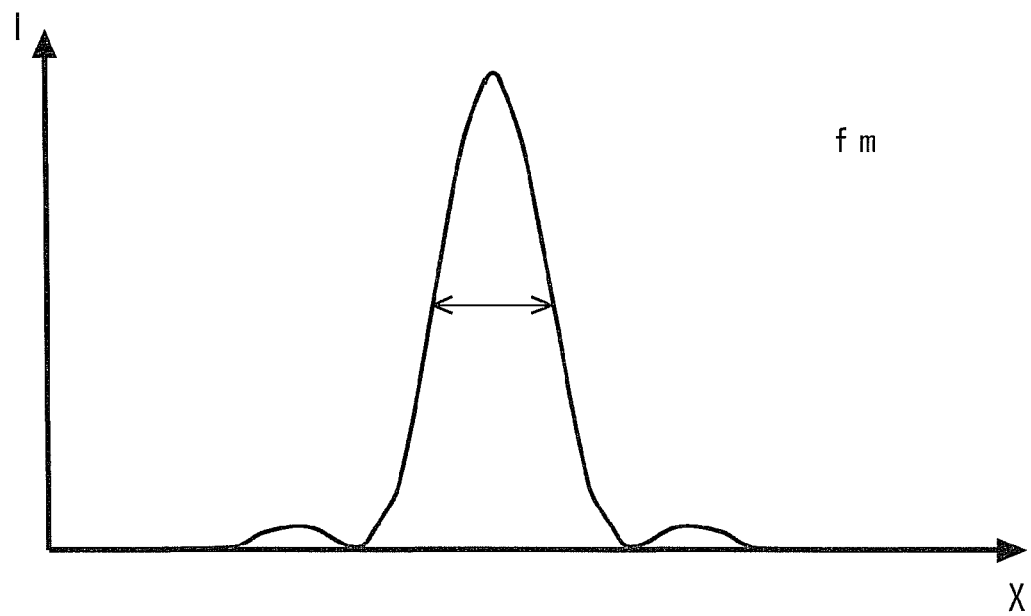
FIG. 6B is a graph schematically showing a spatial distribution of first-order frequency components of reflection light.
Figure 6C:
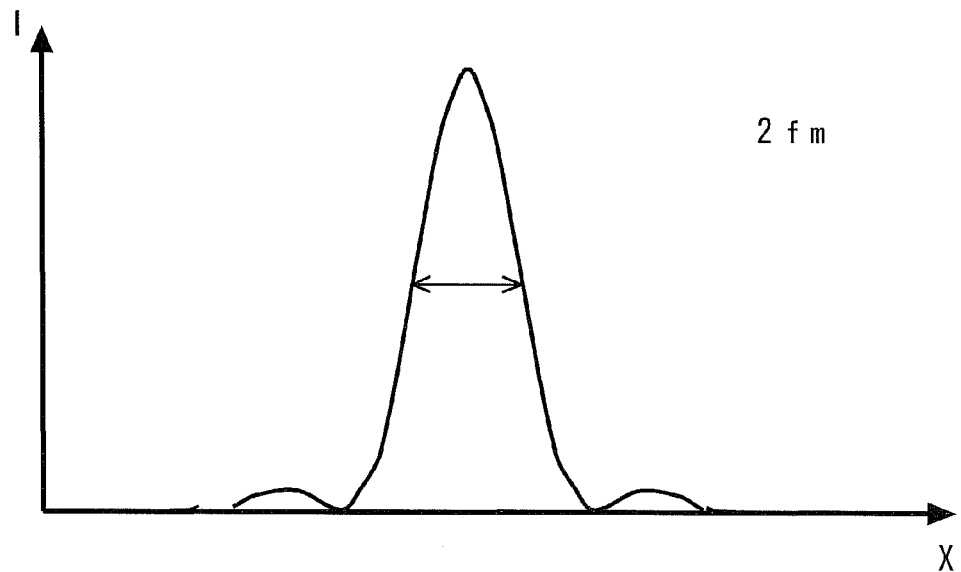
FIG. 6C is a graph schematically showing a signal obtained by demodulating the intensity of reflection light by a second-order harmonic frequency $2f_m$.

Thus, FIGS. 6A to 6C show a spatial distribution of the reflection light having modulation harmonic components and a spatial distribution of the modulation harmonic components. FIG. 6A is a diagram showing a spatial distribution of signal light, which is identical with the spatial distribution indicated by the dashed line of FIG. 2. FIG. 6B shows first-order ($\omega_m$) components, and FIG. 6C shows second-order ($2\omega_m$) components (second-order modulation harmonic components). In FIGS. 6A to 6C, the horizontal axis represents a position and the vertical axis represents light intensity. Note that the vertical axes are illustrated on different scales in the drawings to clarify the explanation.

The spatial distribution shown in FIG. 6B, which shows a first-order component, is proportional to B. The spatial distribution shown in FIG. 6C, which shows a second-order component, is proportional to $B^2$. Accordingly, as shown in FIGS. 6B and 6C, the half-value width of the peak in the spatial distribution of the second-order component is narrower than that of the first-order component. Similarly, an n-order component is proportional to $B^n$. Accordingly, higher-order components have a narrower peak half-value width. In other words, the higher-order components have a narrower peak width and a steeper peak. Accordingly, if higher-order components are detected, each of substantial reflection light spots can be expressed as a power of a point spread function, which improves the spatial resolution. The spatial resolution can be improved in proportion to the order of the detected components. Note that FIG. 6A shows the sum of the first-order component and all modulation harmonic components. The spatial distributions shown in FIGS. 6B and 6C are based on the saturation components of the reflection light. The spatial distribution of the modulation harmonic components varies based on the saturation components of the reflection light. That is, the intensity of the modulation harmonic components varies depending on the intensity of the saturation components of the reflection light. Thus, the spatial resolution can be improved by observing the sample based on the saturation components of the reflection light.

As described above, the saturation degree varies depending on the spatial position on the sample. That is, the saturation degree at the spot center position (x=a) of the laser light is large, and no saturation occurs at the spot end (x=b) of the laser light. At the position between the spot end and the spot center, the saturation degree is smaller than that at the spot center. Accordingly, the amplitude spectrum for the modulation frequency can be obtained by performing Fourier transform on the reflection light intensity at each position as shown in FIGS. 7A to 7C.

Figure 7A:
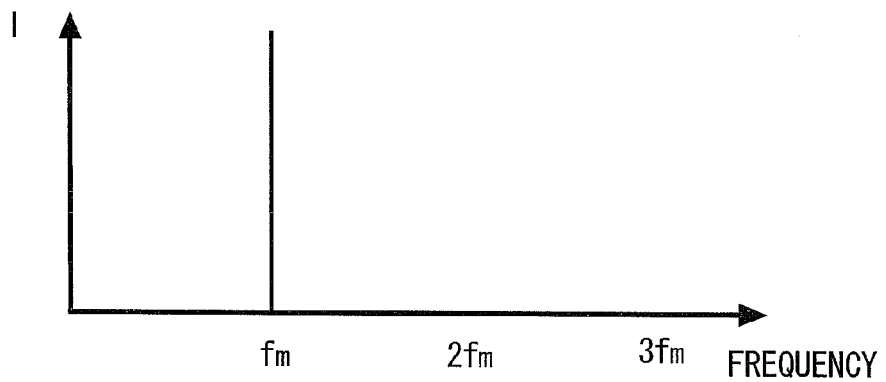
FIG. 7A is a graph schematically showing a power spectrum of reflection light intensity at a spot center.
Figure 7B:
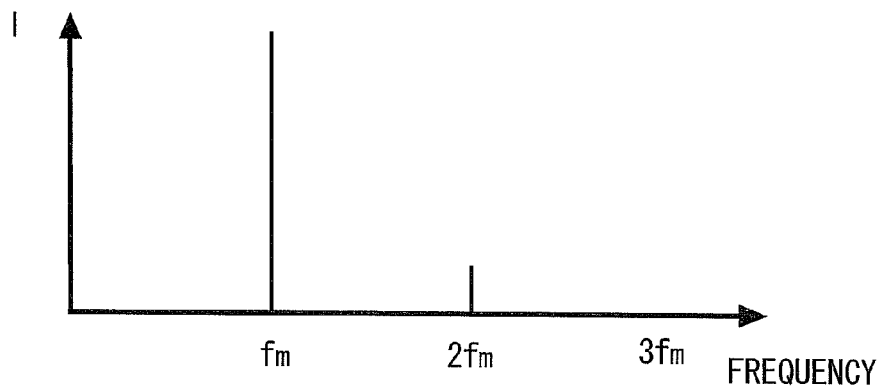
FIG. 7B is a graph schematically showing a power spectrum of reflection light intensity at a spot end.
Figure 7C:
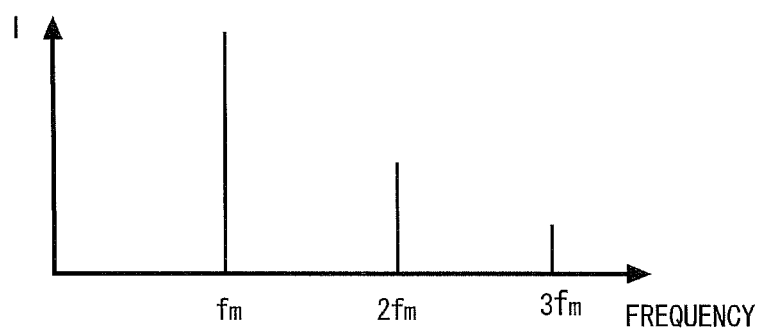
FIG. 7C is a graph schematically showing a power spectrum of reflection light intensity between the center and an end.

FIG. 7A shows the amplitude spectrum at the spot center (x=a). FIG. 7B shows the amplitude spectrum at the spot end (x=b). FIG. 7C shows the amplitude spectrum at the position between the spot center and the spot end. Thus, for example, the resolution can be improved by performing observation according to the signal components having the frequency $2f_m$. The observation may be performed by focusing on the n-order component, as a matter of course. The demodulation with a frequency n times higher than a modulation frequency enables observation with a higher spatial resolution.

Figure 8:
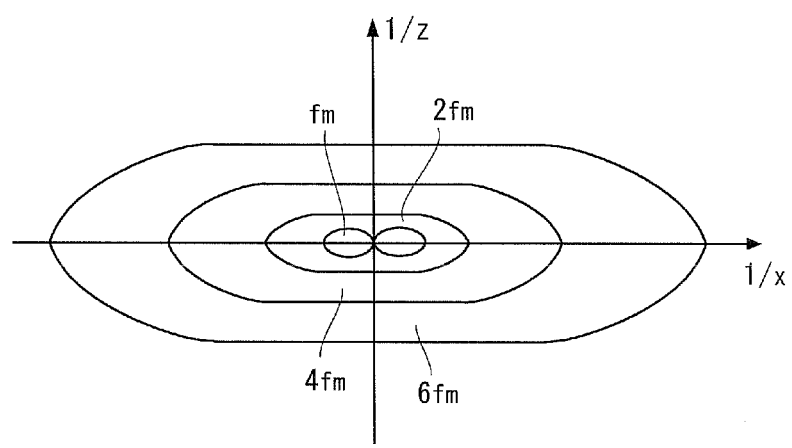
FIG. 8 is a graph showing an optical transfer function obtained when high-order modulation harmonic components are detected.

FIG. 8 shows an example of an optical transfer function obtained when higher-order modulation harmonic components are detected. As shown in FIG. 8, the spatial resolution is increased along with an increase in the order. Note that a combination with a confocal detection method enables further improvement in the spatial resolution. Thus, this embodiment can improve the spatial resolution in all three dimensional directions. Note that a method using a confocal detection method or two-photon response without using the detection method of the present invention is substantially the same as an optical transfer function of $2\omega$.

For example, the detection of the second-order modulation harmonic components enables detection with a spatial resolution twice as high as that when the first-order frequency components are detected. Thus, the detection of the second-order and third-order modulation harmonic components can double or triple the spatial resolution. This enables detection with a spatial resolution beyond the diffraction limit and detection with a resolution higher than that of the laser microscope of the related art. N-fold spatial resolution can be attained by detecting the n-order component, as a matter of course. Further, the reflection light having the laser wavelength $\lambda$ is detected instead of the lost optical harmonics. In other words, the detector 22 receives the reflection light and detects the nonlinear optical loss. Thus, the detection with a high S/N ratio can be attained.

Further, since the reflection light having the same wavelength as that of the illumination light is detected, light having the same wavelength as that of laser light may be detected even in the case of observing the higher-order nonlinear effects. That is, the detection of the fundamental wave enables observation based on the nonlinear effects. Even when the wavelength of the laser light is shortened, the detection can be carried out in a typical optical system. For example, there is no need to propagate light in an ultraviolet region through an optical system, thereby enabling use of a lens, a mirror, and the like of general specifications. In other words, since the nonlinear optical loss is measured, a higher-order nonlinear response can be checked easily without preparing an optical component or measurement instrument for shorter wavelengths. Accordingly, a higher resolution can be achieved while using an optical system for a visible range. The separate detection of the nonlinear response enables three-dimensional observation of the shape of the sample with a spatial resolution beyond the diffraction limit.

As described above, the extraction and detection of n-order (n is a natural number of 2 or more) components improves the spatial resolution. Thus, the lock-in amplifier 23 performs lock-in detection at a fixed predetermined frequency. Assume herein that the detection frequency of the lock-in amplifier 23 is n times (n is a natural number of 2 or more) higher than the modulation frequency $f_m$. Further, the lock-in amplifier 23 locks in a phase at which the illumination light peaks to thereby perform detection. This enables high-sensitivity detection as well as detection of higher-order modulation harmonic components. Accordingly, the spatial resolution can be further improved. Since the detection frequency is an integral multiple of the modulation frequency $f_m$ of laser light, electrically filtering the frequency band enables extraction of the modulation harmonic components with an extremely high sensitivity. Note that not only the lock-in detection, but also the detection of modulation harmonics using a high-pass filter can be attained.

Assume that the modulation frequency $f_m$ of the modulator 11 is much higher than that for scanning of the sample 17. That is, the modulation frequency is increased such that a plurality of peaks appears in a scanning time of an optical image corresponding to one pixel. For example, when a scanning time corresponding to one pixel of the optical image is 1 msec, a modulation frequency is set to 100 kHz. In this case, 100 peaks of the laser light appear in the scanning time of one pixel. The modulation frequency is set higher than the scanning frequency of the sample, thereby increasing the number of times of saturation occurring in the scamming time of one pixel to perform detection precisely.

According to the present invention, as the saturation degree increases, the saturation can be easily detected and the resolution can be improved. However, if the laser light intensity (density) is increased to increase the laser light intensity, there is a possibility that the sample is damaged. In this case, a pulse laser light source is preferably used as the light source. In this case, for example, a cosine function takes an envelope curve as indicated by the dotted line of FIG. 3, and laser light has a pulse intensity corresponding to the envelope curve. The use of the pulse laser light source enables reduction in the total irradiation amount, while achieving the light intensity (density) that reaches the saturation. Hence, it is possible to prevent the sample from being damaged. Assume herein that the repetition frequency of the pulse laser light is set much higher than the modulation frequency. That is, the frequencies are set such that a plurality of pulses appears in one modulation period. For example, when the modulation frequency is 100 kHz, a repetition frequency of 80 MHz can be used. In this case, 800 pulses are included in one period. In this way, precise detection is realized by setting the repetition frequency of the pulse laser light higher than that of the modulation frequency.

Note that any function other than the cosine function can be used as the function for modulating the intensity of laser light, as long as the function has a periodic function. Here, the laser light intensity is set to an intensity at which saturation of signal light occurs at the timing when the maximum laser light intensity is obtained. That is, at the timing at which the maximum laser light is obtained, the saturation of signal light occurs, and the sample needs only to be irradiated with laser light in a nonlinear range where the laser light and signal light have a nonlinear relation.

The laser microscope according to this embodiment may also have a configuration with no confocal optical system. That is, an optical microscope other than a confocal microscope may also be used by removing the pinhole 21. Since the intensity of laser light from positions other than a focus position is low, the degree of saturation of the signal light is small. That is, at positions other than the focus position, the intensity of the laser light is low and the signal light has the linear region which is not the nonlinear region. Accordingly, the saturation components of the signal light from positions other than the focus position are reduced. This results in improvement of the resolution in a Z-direction also in the configuration with no confocal optical system. That is, the signal light has the linear region at a position shifting from the focus position in the optical axis direction. Therefore, the saturation of the signal light does not occur, which makes it possible to extract information only from the focus position and its vicinity. This enables three-dimensional observation with a simple configuration without using any confocal optical system. Needless to say, the resolution can be further improved by using a laser microscope including a confocal optical system.

Though the reflection light is detected in the above description, light transmitted through a sample may be detected. In this case, the detector 22 is disposed on the opposite side of the objective lens 16. Also in this case, laser harmonic components and fundamental frequency components of the transmitted light are separated using a wavelength difference. Furthermore, observation based on scattered light (Rayleigh scattering, Mie scattering) may also be carried out. Accordingly, the present invention can also be achieved by optical microscopes having a configuration other than the configuration shown in FIG. 1. That is, though the description has been made using an epi-illumination type laser microscope in FIG. 1, the present invention can also be applied to a transmitted-light illumination type optical microscope. In the case of measuring transmitted light or scattered light, the above-described technique is used for the transmitted-light illumination type optical microscope. The transmitted light and scattered light may be detected simultaneously, as a matter of course. Also in the case of performing observation based on reflection light or scattered light, the above-described technique is used for the epi-illumination type optical microscope.

Second Embodiment

In this embodiment, observation is performed based on saturation components of signal light generated due to a nonlinear optical effect. For example, scattered light or the like generated in a sample due to the nonlinear optical effect is detected. In this case, scattered light having a wavelength different from a laser wavelength is detected. For example, various types of light generated by hyper-Rayleigh scattering, harmonic generation, Raman scattering, coherent anti-Stokes Raman scattering (CARS), four-wave mixing, stimulated emission, difference frequency generation, sum frequency generation, parametric fluorescence, or stimulated Raman scattering (SRS), for example, may be detected. The scattered light includes scattered light generated due to the nonlinear optical effect. The generation of the nonlinear optical effect or other optical effects causes a loss in light intensity, that is, a harmonic loss. The term "harmonic loss" herein described refers to a harmonic loss in signal light, which is a concept different from a harmonic loss in laser light (fundamental wave). This harmonic loss is a nonlinear optical loss (hereinafter referred to as "nonlinear optical loss").

In the case of detecting scattered light or the like having a wavelength different from that of incident laser light, the light having the laser wavelength is prevented from entering the detector 22. In other words, the light having the laser wavelength is separated from the laser harmonics by using a wavelength difference. In this case, for example, an optical filter, such as a band-pass filter, or a dichroic mirror is used. That is, in the case of detecting scattered light (Raman scattering, hyper-Rayleigh scattering, stimulated Raman scattering, coherent anti-Stokes Raman scattering, harmonic generation, parametric fluorescence, four wave mixing, stimulated emission, sum frequency generation, difference frequency generation, etc.) having a wavelength different from the laser wavelength, for example, the laser light (fundamental wave) and the signal light are separated using a wavelength difference. For example, an optical filter, such as a band-pass filter, or a dichroic mirror is used. An optical element that blocks the laser light is disposed between the detector and the sample. Note that in the case of detecting scattered light, the light source 10 may be disposed on the opposite side of the objective lens 16. That is, the scattered light transmitted through the sample 17 may be detected on the opposite side of the light source 10.

In this manner, the scattered light or the like from the sample is detected by the detector 22 as signal light emitted from the sample. Then, the observation may be performed using the modulation harmonic components of the modulator 11. Also in this embodiment, the modulation may be performed with second or higher-order modulation frequency. Further, selection of a frequency to be demodulated prevents the laser light intensity, which causes saturation of the non-linear optical loss, from increasing. In this case, the frequency to be demodulated varies depending on the type of light to be detected. For example, in the case of the multi-photon reaction, the second-order component (frequency $2f_m$) appears also in the linear region. Accordingly, it is desirable to perform demodulation with third or higher-order modulation harmonics. A preferable demodulation frequency will be described below with reference to FIGS. 9A to 9D.

(Regarding One-Photon Reaction)

Figure 9A:
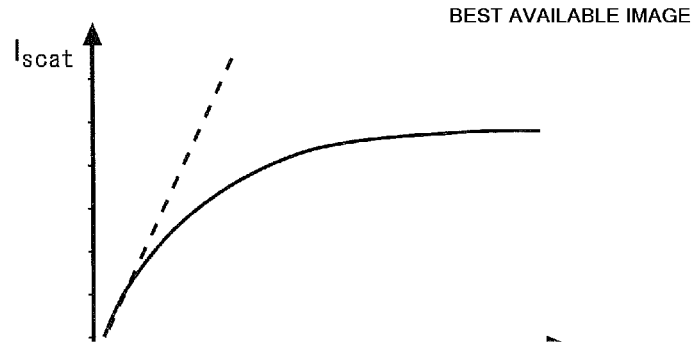
FIG. 9A is a graph showing a relation between laser light and scattered light.

First, FIG. 9A shows a relation between a laser light intensity and a scatter light intensity in a one-photon reaction, that is, a linear response, as illustrated in the first embodiment. In FIG. 9A, the horizontal axis represents a laser light intensity $I_{ex}$ and the vertical axis represents a scattered light intensity $Is_{cat}$. Note that the scattered light shown in FIG. 9A is scattered light having the same wavelength as the laser wavelength. For example, Rayleigh scattered light or Mie scattered light is output due to the one-photon reaction. That is, the scattered light is obtained by a linear optical effect. When there is no saturation, the laser light and scattered light linearly change. Then, when the laser light intensity is increased, saturation of the scattered light occurs. In this case, the scattered light serves as a first-power response corresponding to the first power of the laser light intensity to be modulated.

In the case of signal light generated by the linear optical effect, the relation between the laser light and the signal light is obtained as shown in FIG. 9A. That is, the scattered light, reflection light, or transmitted light having the same wavelength as the laser wavelength has a relation as shown in FIG. 9A. In this case, as described above, the observation is performed using second or higher-order modulation harmonics. For example, the detected light detected by the detector 22 is demodulated with the frequency $2f_m$. In other words, the lock-in frequency of the lock-in amplifier 23 is set to $2f_m$. Further, in this case, the signal light having the same wavelength as the laser light wavelength is detected and the light having a wavelength other than the laser light wavelength is removed by the filter 19.

(Regarding Two-Photon Reaction)

Figure 9B:
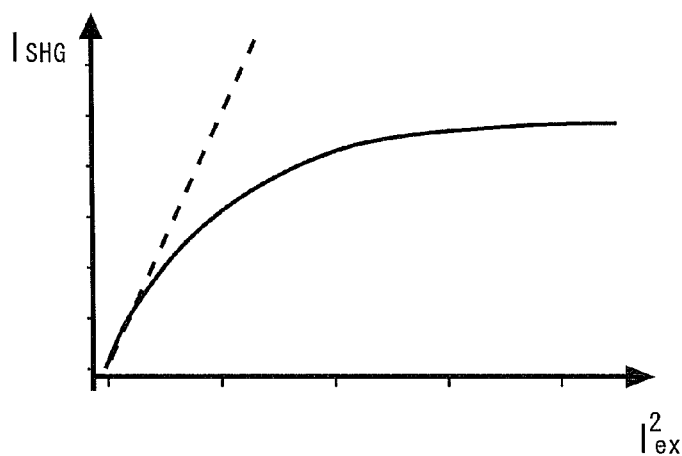
FIG. 9B is a graph showing a relation between laser light and second harmonics.

On the other hand, FIG. 9B shows a relation between laser light and signal light in a two-photon reaction which is a nonlinear optical effect. FIG. 9B shows the case where the signal light is generated by second harmonic generation (SHG). In FIG. 9B, the horizontal axis represents the laser light intensity $I_{ex}$ and the vertical axis represents a second harmonic intensity $I_{SHG}$. The second harmonic generation is a response due to a two-photon reaction. That is, the second harmonic generation (SHG) is a square response corresponding to the square of the laser light intensity to be modulated. When there is no saturation, the square of the intensity-modulated laser light (modulated light) and the second harmonic (optical harmonics) linearly change. Then, when the laser light intensity is increased, SHG saturation occurs. For example, when the laser light intensity $I_{ex}$ is proportional to $(1+\cos(\omega_m t))$ in the linear region in which the SHG saturation does not occur, the SHG intensity $I_{SHG}$ is proportional to $(1+\cos(\omega_m t))^2$. When this expression is developed, the following expression is obtained.

$$I_{SHG}=1+2\cos(\omega_m t)+\cos^2(\omega_m t) \quad (1)$$

Note that in the above expression (1) and the following expression (2), a proportional coefficient is set to "1" so as to simplify the explanation. When $\cos^2(\omega_m t)$ is transformed using $\cos(2\omega_m t)$, the following expression (2) is obtained.

$$I_{SHG}=1+2\cos(\omega_m t)+(1+\cos(2\omega_m t))/2 \quad (2)$$

Accordingly, in the case of the SHG, which is a square response, non-saturation components (linear components) of the SHG include the first-order component as well as the second-order component. In the SHG, the first-order component ($f_m$) and the second-order modulation harmonic component ($2f_m$) are present for the modulation frequency ($f_m$) of the laser light. That is, the SHG intensity in the linear region also includes the second-order modulation harmonic component.

In this case, the observation is performed using third or higher-order components. For example, the detected light detected by the detector 22 is demodulated with the frequency $3f_m$. In other words, the lock-in frequency of the lock-in amplifier 23 is set to $3f_m$. Further, in this case, signal light having a wavelength twice as long as the wavelength of laser light is detected, and the light having the same wavelength as that of the laser light and the light of third or higher-order laser harmonics are removed by the filter 19.

(Regarding Coherent Anti-Stokes Raman Scattering)

Figure 9C:
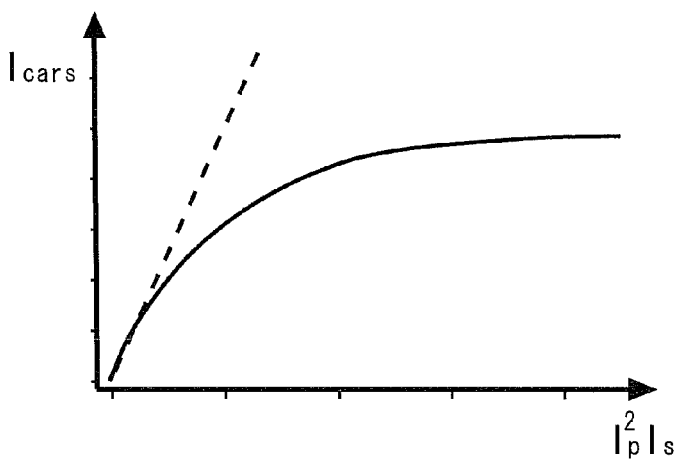
FIG. 9C is a graph showing a relation between incident light and CARS light.

Next, an intensity $I_{CARS}$ of coherent anti-Stokes Raman scattered light will be described with reference to FIG. 9C. In the case of generating coherent anti-Stokes Raman scattered light, pump light and Stokes light are applied. That is, two laser beams are simultaneously applied to the same position of the sample by using two laser light sources. The pump light has a wavelength different from that of the Stokes light. Assume herein that Ip represents the pump light intensity and Is represents the Stokes light intensity. In this case, the CARS light intensity $I_{CARS}$ is proportional to $Ip^2 Is$ in the linear region in which the CARS light is not saturated.

Accordingly, when the pump light intensity Ip is modulated and the Stokes light intensity Is is not modulated, the Stokes light intensity Is is constant. Thus, the square response is obtained in which the CARS light intensity $I_{CARS}$ varies depending on the square ($Ip^2$) of the pump light to be modulated. In this case, the observation is performed using third or higher-order components, as in the case of second harmonics (optical harmonics) described with reference to FIG. 9B. For example, the detected light detected by the detector 22 is demodulated with the frequency $3f_m$. In other words, the lock-in frequency of the lock-in amplifier 23 is set to $3f_m$.

On the other hand, when the Stokes light intensity Is is modulated without modulating the pump light intensity Ip, the pump light intensity Ip is constant. Accordingly, the first-power response is obtained in which the CARS light intensity $I_{CARS}$ varies depending the first power (Is) of the intensity-modulated Stokes light. Accordingly, the observation is performed using second or higher-order modulation harmonics, as in the case of scattered light described with reference to FIG. 9A. For example, the detected light detected by the detector 22 is demodulated with the frequency $2f_m$. In other words, the lock-in frequency of the lock-in amplifier 23 is set to $2f_m$.

Needless to say, both the pump light intensity Ip and the Stokes light intensity Is may be modulated. In this case, when the pump light intensity Ip and the Stokes light intensity Is are modulated with the same frequency $f_m$, the observation is performed using fourth or higher-order components (frequency $4f_m$). In the case of modulating both the pump light intensity I and the Stokes light intensity Is with the same modulation frequency, the intensities are preferably modulated at the same phase. That is, it is preferable to match the timings at which two light beams are applied to the sample with a maximum intensity.

Alternatively, the pump light intensity Ip and the Stokes light intensity Is may be modulated with different frequencies. When the intensities are modulated with different frequencies, the intensities are demodulated with an integral multiple of a frequency corresponding to the difference or sum between two frequencies. For example, assuming that $f_{m\_p}$ represents the modulation frequency of the pump light and $f_{m\_s}$ represents the modulation frequency of the Stokes light, the intensities are demodulated with a frequency n $(2f_{m\_p}-f_{m\_s})$ corresponding to an integral multiple of the difference or with a frequency n $(2f_{m\_p}+f_{m\_s})$ corresponding to an integral multiple of the sum.

(Regarding Stimulated Raman Scattering)

Figure 9D:
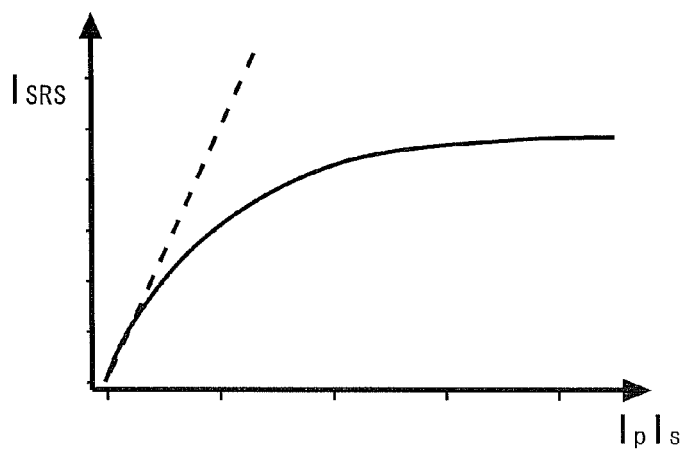
FIG. 9D is a graph showing a relation between incident light and stimulated Raman scattered light.

A stimulated Raman scattered light intensity $I_{SRS}$ will be described with reference to FIG. 9D. In the case of generating stimulated Raman scattered light, pump light and Stokes light are applied. That is, two laser beams are simultaneously applied to the same position of the sample by using two laser light sources. The pump light has a wavelength different from that of the Stokes light. Assume herein that Ip represents the pump light intensity and Is represents the Stokes light intensity. In this case, the stimulated Raman scattered light intensity $I_{SRS}$ is proportional to IpIs in the linear region in which the signal light is not saturated. Accordingly, in the case of modulating one of the pump light intensity I and the Stokes light intensity Is, the first-power response of the intensity-modulated laser light is obtained. Accordingly, the observation is performed using second or higher-order components, as in the case of scattered light described with reference to FIG. 9A. Further, in the case of modulating both the pump light intensity I and the Stokes light intensity Is with the same modulation frequency, the square response is obtained. Accordingly, the observation is performed using third or higher-order modulation harmonics. In the case of modulating both the pump light intensity I and the Stokes light intensity Is with the same modulation frequency, the intensities are preferably modulated at the same phase. That is, it is preferable to match the timings at which two light beams are applied to the sample with the maximum intensity.

Alternatively, the pump light intensity Ip and the Stokes light intensity Is may be modulated with different modulation frequencies. When the intensities are modulated with different modulation frequencies, the intensities are demodulated with an integral multiple of a frequency corresponding to the difference or sum between two frequencies. For example, assuming that $f_{m\_p}$ represents the modulation frequency of the pump light and $f_{m\_s}$ represents the modulation frequency of the Stokes light, the intensities are modulated with the difference n $(f_{m\_p}-f_{m\_s})$ or the sum n $(f_{m\_p}+f_{m\_s})$. Note that in the case of modulating both the pump light intensity I and the Stokes light intensity Is, the intensities are preferably modulated at the same phase. Thus, in the case of making the two laser beams incident, the intensities are demodulated with a frequency corresponding to the sum or difference between an integral multiple of a first modulation frequency and an integral multiple of a second modulation frequency.

In this manner, the order of the demodulation frequency for achieving the high-resolution observation is selected depending on the order of the intensity-modulated laser light. In a nonlinear optical reaction such as a multi-photon reaction, the intensity-modulated laser light is desirably demodulated with an order higher than the order at which the intensity-modulated laser light contributes to the signal light intensity. For example, assume that when the modulated laser light intensity is raised to the n-th power, the linear region can be achieved. That is, assuming that $I_m$ represents the modulated laser light intensity and I represents the signal light intensity, the laser light intensity is proportional to the n-power ($I_m^n$) of $I_m$ in the linear region. In this case, the demodulation is preferably performed with an order of (n+1) which is higher by one order. Thus, the selection of the order for the demodulation expands the observation technique according to the present invention to the complicated multi-photon reaction, and prevents an increase in the laser light intensity.

Specifically, when the intensity of only one laser beam is modulated in a configuration for applying one laser beam or applying two or more laser beams, the demodulation frequency is selected depending on the order of the response for generating the signal light (scattered light). That is, when the signal light from the sample is generated by an n-photon reaction (n is a natural number of 1 or more) of the intensity-modulated laser light, (n+1) or higher-order modulation harmonic components for the modulation frequency are extracted to thereby perform observation. For example, in the case of the one-photon reaction, two or more modulation harmonic components are preferably extracted, and in the case of the two-photon reaction, three or more modulation harmonic components are preferably extracted. This enables observation with a high resolution.

Also in the fluorescence disclosed by Patent Literature 1, the demodulation is performed with a third-order modulation frequency in the case of detecting two-photon fluorescence, and the demodulation is performed with a fourth-order modulation frequency in the case of detecting three-photon fluorescence.

Also in the case of modulating the intensity of two or more laser beams with the same modulation frequency in the configuration for applying two or more laser beams, the demodulation frequency is changed depending on the sum of the orders of responses for generating the signal light (scattered light). That is, when the signal light from the sample 17 is generated by an m-photon reaction (m is a natural number of 2 or more) of two intensity-modulated laser beams, (m+1) or higher-order modulation harmonic components for the modulation frequency are extracted to thereby perform observation. In other words, in the case of using two laser beams, the demodulation is preferably performed with an order greater than the number of photons (total number of photons) of the two laser beams which contribute to the nonlinear optical effect. This enables observation with a high resolution without increasing the laser light intensity. For example, in the CARS light, the two-photon reaction of pump light and the one-photon reaction of Stokes light are obtained. In the case of detecting the CARS light by modulating each of the pump light and the Stokes light, a (2+1)=three-photon reaction is obtained. Accordingly, the demodulation is preferably performed with a fourth or higher-order modulation frequency. Note that in the case of modulating the intensities of two laser beams and irradiating the sample with the two laser beams, the intensity modulation is preferably performed at the same phase.

Next, the saturation of the nonlinear optical loss will be described. When the laser light intensity is set to an extremely high level, saturation occurs also in the nonlinear optical loss caused by the second harmonics (optical harmonics) shown in FIG. 4. That is, the second harmonics (optical harmonics) themselves are saturated. In this case, the nonlinear optical loss is generated due to the third-order harmonics (optical harmonics) or high-order optical harmonics. Accordingly, as the laser light intensity is set to an extremely higher level, the second-order modulation harmonic components decrease. Such a higher-order nonlinear optical loss will be described with reference to FIG. 10.

Figure 10:
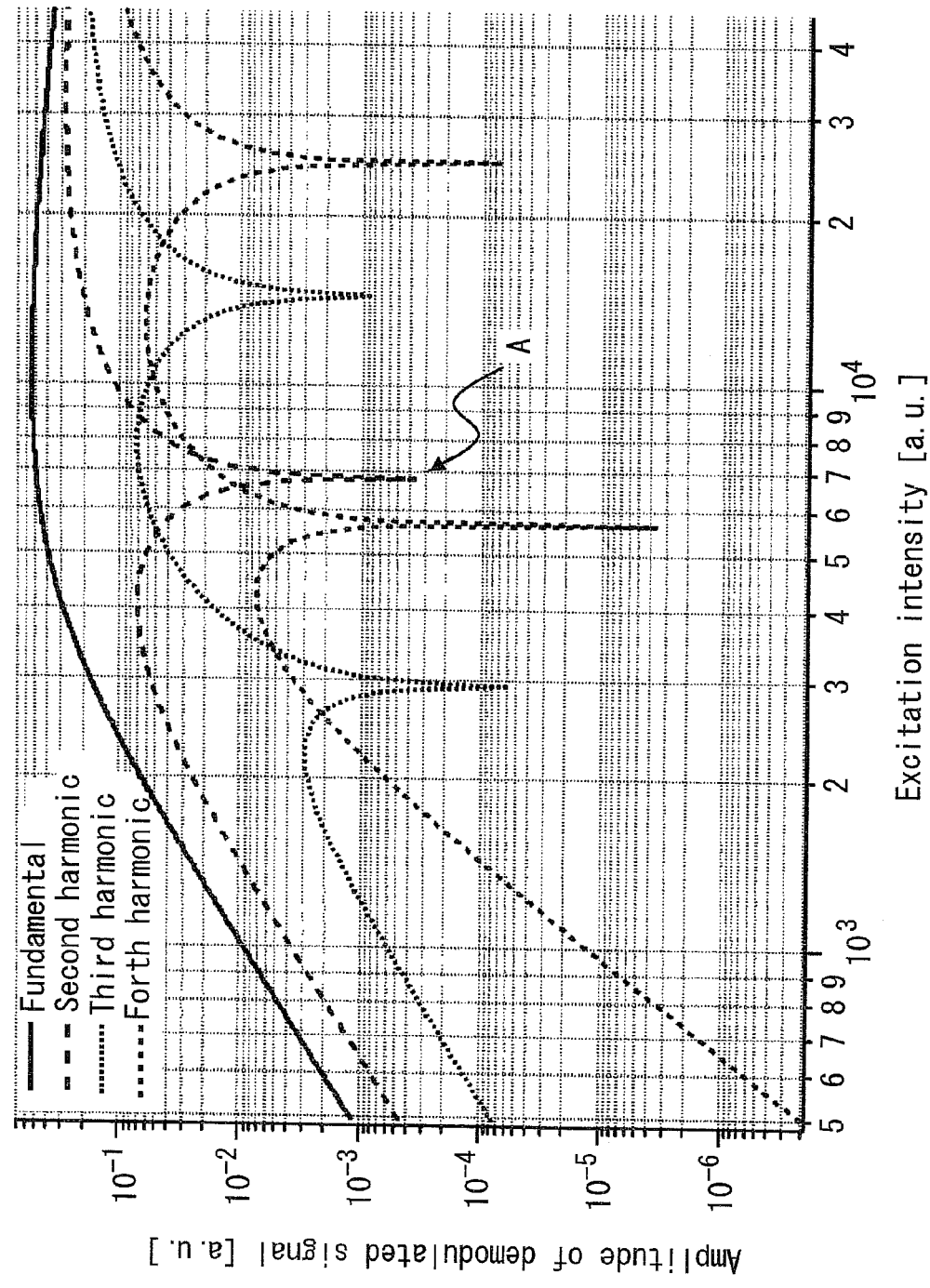
FIG. 10 is a graph showing demodulated signals with respect to incident light intensity.

FIG. 10 is a graph showing simulation results obtained by calculating first-order to fourth-order components $\omega_m$ to $4\omega_m$ in a three-photon reaction such as third harmonic generation. In FIG. 10, the horizontal axis represents incident light intensity and the vertical axis represents demodulated signal, that is, signal light intensity for each modulation harmonic component (including the first order). Saturation components of the signal light appear in this demodulated signal. In FIG. 10, the first-order to fourth-order components are respectively represented by (Fundamental), (Second harmonic), (Third harmonic), and (Forth harmonic).

In the case of the three-photon reaction, as described above, a third-order component appears also in the linear region in which the signal light is not saturated. Accordingly, in the linear region, the second-order and third-order components increase at substantially the same inclination according to the incident light intensity. In the nonlinear region in which the saturation occurs, the fourth-order component appears. A rise of the fourth-order component is caused by the saturation of the second-order and third-order components. The fourth-order component is also saturated. In this case, a fifth-order or sixth-order component appears. That is, the nonlinear optical loss of the fourth-order component appears as the fifth-order or sixth-order component (not shown in FIG. 10).

Furthermore, an inverse peak (for example, "A" point in FIG. 10) appears in the second-order component and the like in FIG. 10. The term "inverse peak" refers to a point where the intensity decreases steeply. In practice the inventors of this application have found that the intensity rapidly decreases to the vicinity of "0" at this inverse peak.

Figure 11:
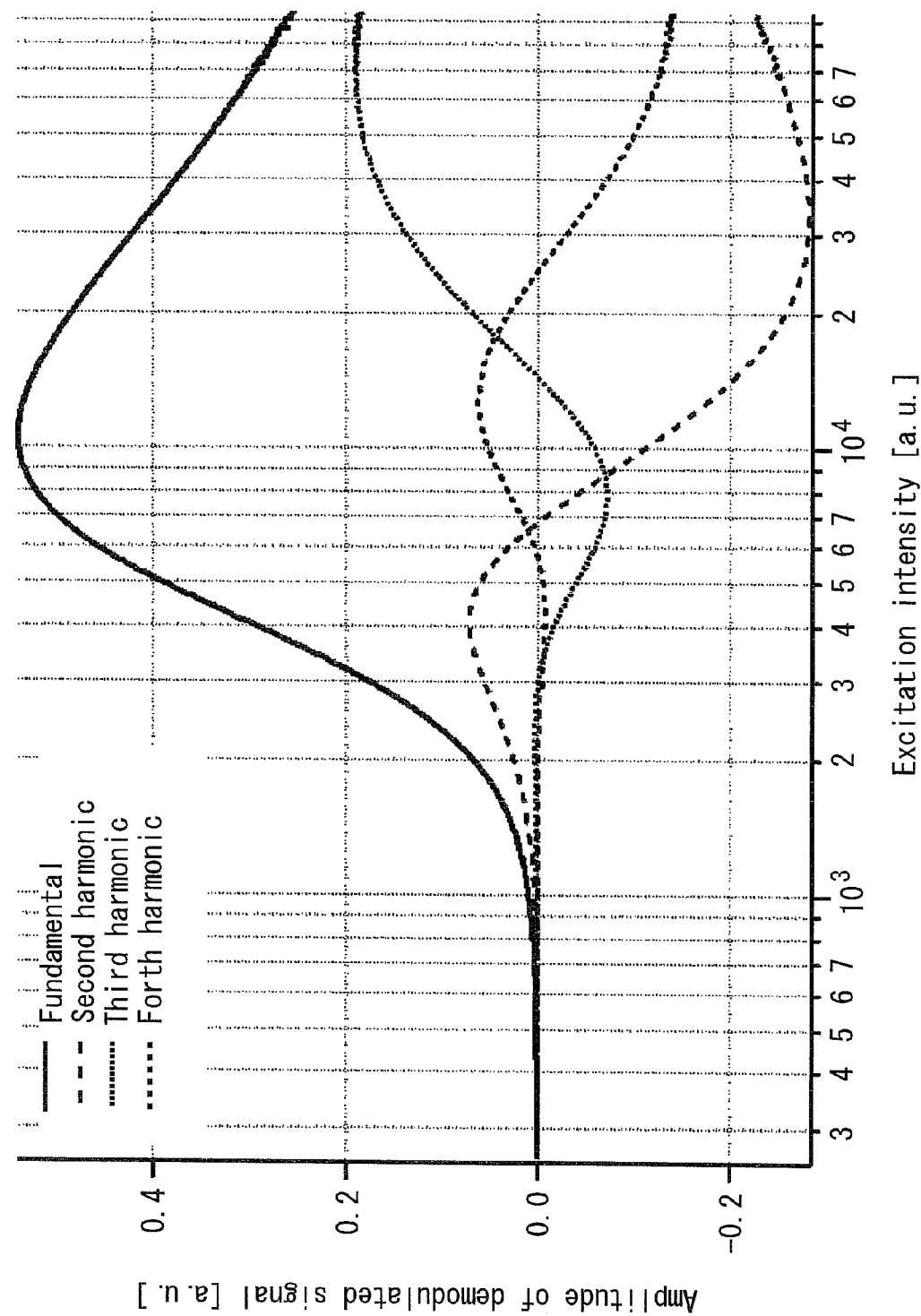
FIG. 11 is a graph showing demodulated signals with respect to incident light intensity.

FIG. 11 shows demodulated signals obtained by changing the scale. FIG. 11 shows the first-order to fourth-order components. As shown in FIG. 11, the second-order to fourth-order modulation components take negative values, and the phases are different for each order.

Thus, the intensity of the modulation component greatly varies depending on the intensity of the incident light (excitation light). That is, even when the laser light intensity is increased, the laser light intensity at which saturation of the modulation harmonic component does not occur is present. Accordingly, a saturation component of a certain order does not appear in the laser light intensity corresponding to the inverse peak. Further, at a certain laser light intensity, the phase of the modulation harmonic component may be reversed and the modulation harmonic component may take a negative value. Thus, when the laser light intensity is set so as to include the intensity corresponding to the inverse peak, the point spread function greatly varies.

Here, the inverse peak is set to be included in the range of the laser light intensity to be modulated. In this case, the point spread function greatly varies. Simulation results obtained by calculating this point spread function will be described with reference to FIGS. 12 and 13.

Figure 12:
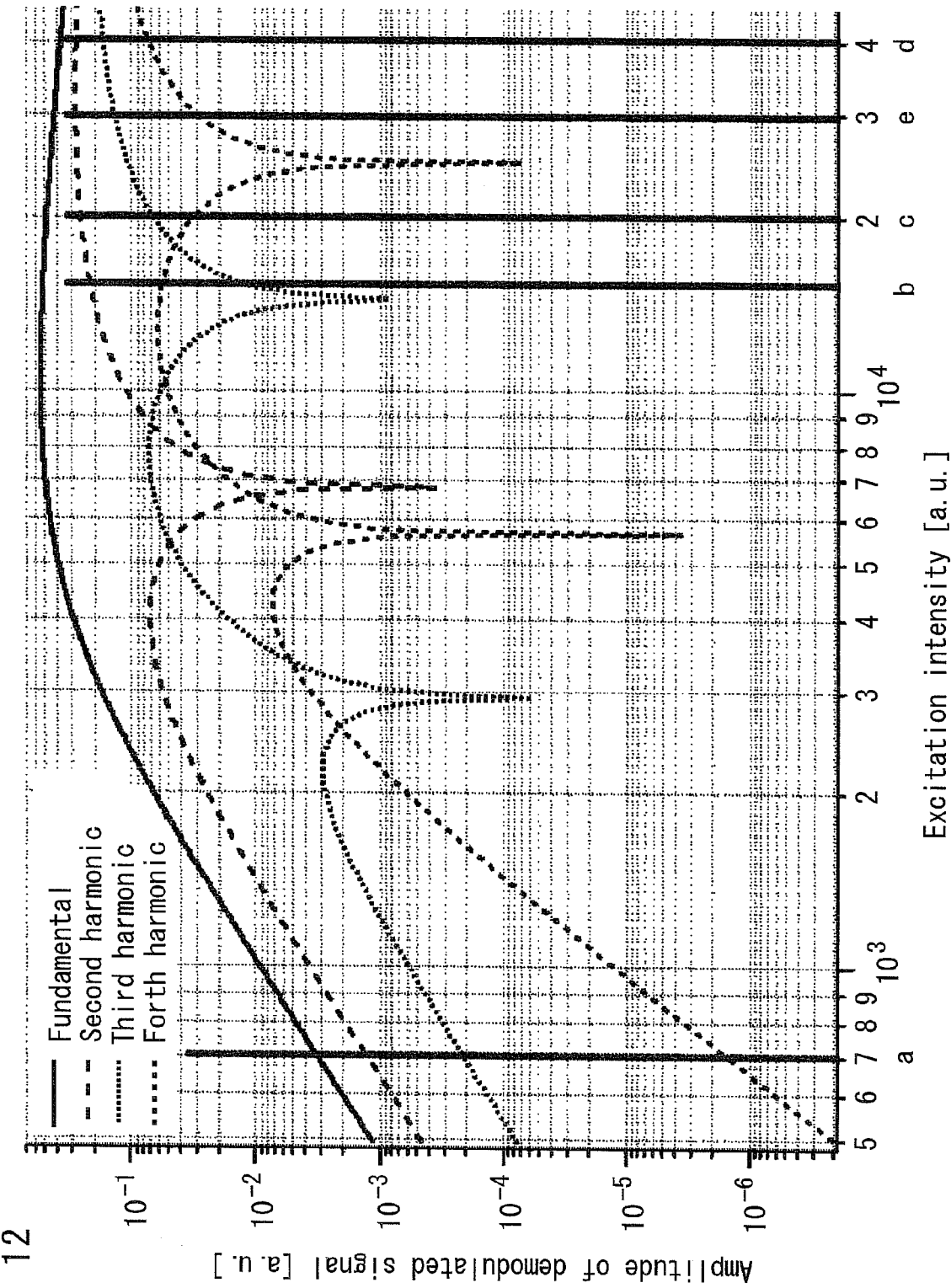
FIG. 12 is a graph showing demodulated signals with respect to incident light intensity.

FIG. 12 is a graph showing demodulated signals with respect to incident light intensity, and corresponds to FIG. 10. FIG. 12 shows the first-order to fourth-order components and the total components. Note that certain five incident light values are respectively represented by a, b, c, d, and e as indicated by dashed lines and solid lines in the longitudinal direction of FIG. 12 to describe the range of the incident light intensity (laser light intensity) to be modulated. As is seen from FIG. 12, the incident light intensities increase in the order of d, e, c, b, and a.

First, FIG. 13a shows the point spread function obtained when the intensity modulation is performed such that the maximum laser light intensity is set to "a". In this case, the modulation range of the incident light intensity is "0" to "a". Note that FIG. 13a shows the point spread function of the first-order component.

Figure 13:
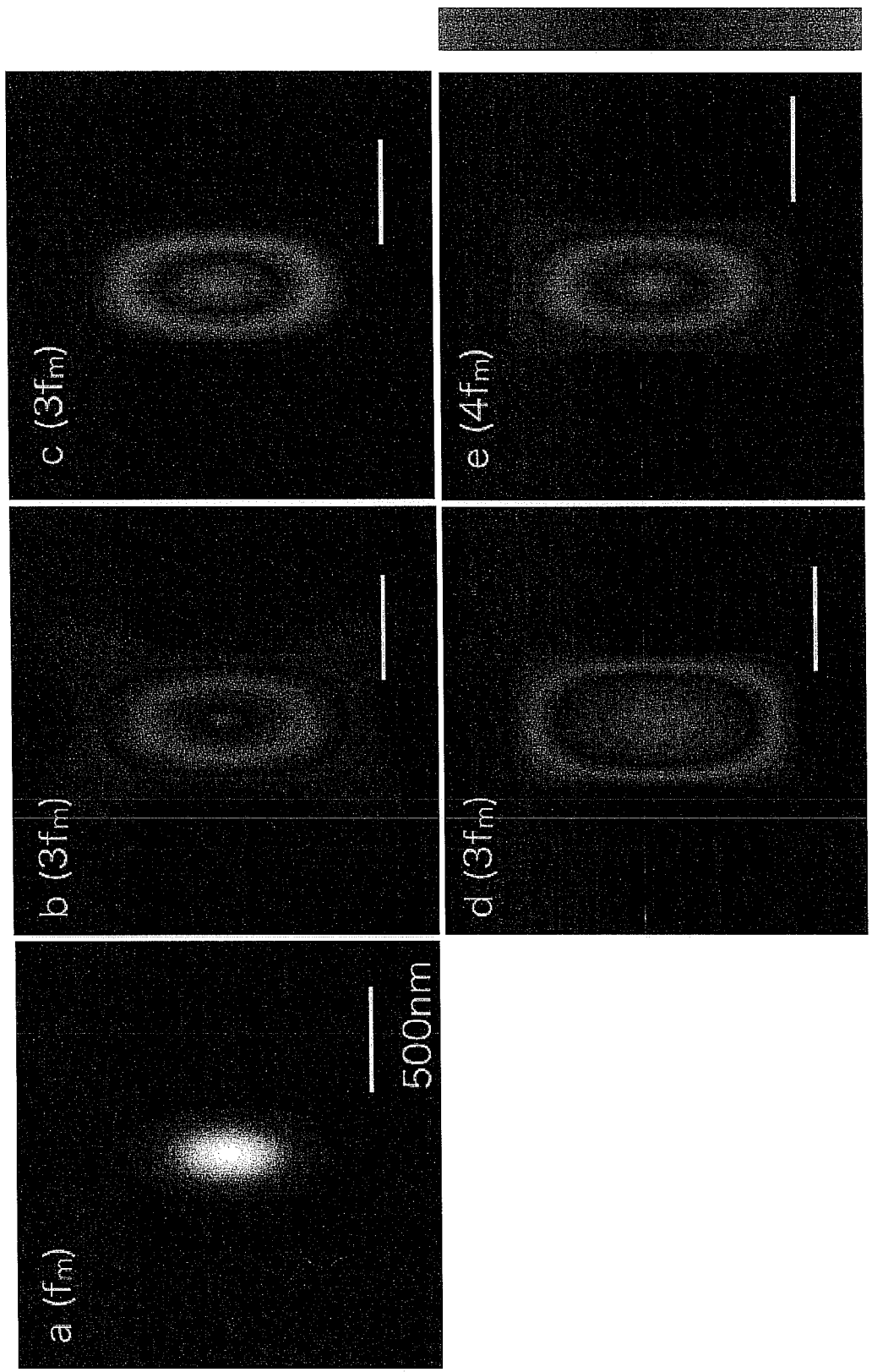
FIG. 13 is a diagram showing point spread functions obtained when a modulation range of incident light intensities is changed.

Next, a description is made of the case where the maximum value of the laser light intensity is "b". In this case, the modulation range of the incident light intensity is "0" to "b". The point spread function of the third-order component is indicated by "b" in FIG. 13. At the center position of the laser light spot, the incident light intensity becomes the maximum "b". As shown in FIG. 12, the incident light intensity slightly smaller than the laser light intensity "b" corresponds to the inverse peak of the third-order component. Thus, at positions slightly apart from the center position of the laser light spot, saturation of the third-order component does not occur. In other words, at positions slightly apart from the spot, the saturation of the third-order component decreases. Accordingly, each point spread function in the vicinity of the spot center takes a minimum value. The minimum value shows a ring shape as shown in FIG. 13b.

Next, FIG. 13c shows the point spread function of the third-order component obtained when the intensity modulation is performed such that the incident light intensity has the maximum value "c". Similarly, FIG. 13d shows the point spread function of the third-order component obtained when the intensity is modulated such that the incident light intensity has the maximum value "d". As shown in FIGS. 13b to 13d, the third-order point spread function varies depending on the modulation range. When the laser light intensity is increased so as to obtain the modulation range including the inverse peak, the point spread function of the third-order component has a ring-shaped minimum value. The position of the minimum value from the spot center varies depending on the relation between the modulation range and the inverse peak. In this manner, the point spread function varies depending on the modulation range of the incident light intensity. In practice, an image to be observed is represented by a combination of various point spread functions. Accordingly, an image analysis is performed from this point of view to thereby improve the resolution.

Next, FIG. 13e shows the point spread function of the fourth-order component obtained when the intensity modulation is performed such that the incident light intensity has the maximum value "d". In this case, the minimum value is obtained at the spot center, and the ring-shaped maximum value is present around the spot center. Further, the ring-shaped minimum value is present outside the ring-shaped maximum value. Accordingly, the point spread function can be substantially reduced. This contributes to an increase in the spatial resolution as compared to the demodulation with the third-order modulation frequency.

Figure 14:
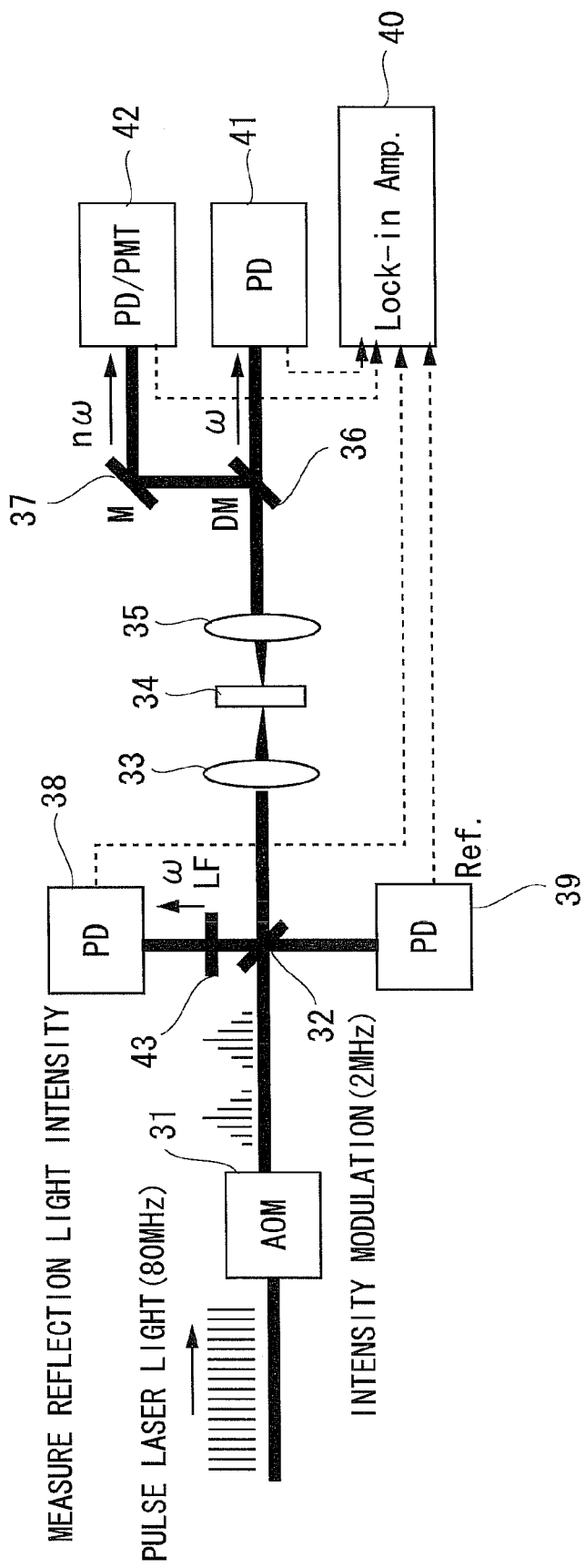
FIG. 14 is a diagram showing a specific configuration example of a laser microscope according to an embodiment of the invention.

Next, a specific configuration example of the above-described laser microscope that detects saturation of signal light will be described. FIG. 14 is diagram showing a configuration for detecting transmitted light/scattered light transmitted through a transparent sample 34 and reflection light/scattered light from the sample 34. In FIG. 14, a pulse laser light source (omitted in FIG. 14) having a repetition frequency of 80 MHz is used. In this case, an ultra-short pulse laser light source having a wavelength of 1200 nm is used as the light source. Needless to say, the laser light source can be changed depending on the sample. The laser light source is a mode-locked Ti:sapphire laser+OPO (light parametric oscillator), and has a pulse width of, for example, 200 fsec. Further, nonlinear optical crystal such as BBO or LBO is used as the sample 34. Note that in FIG. 14, the transmitted light is detected by a non-confocal optical system. In the configuration shown in FIG. 14, observation is performed using both the nonlinear optical loss and the harmonic generation.

Then, a modulator 31 modulates the intensity of the laser light. The modulator 31 is an AOM (acousto-optical modulator), for example, and modulates the intensity with a single frequency (for example, 2 MHz). The modulation frequency is set much lower than the repetition frequency of the pulse of the laser light. The laser light modulated by the modulator 31 enters a beam splitter 32. A part of the light is transmitted through the beam splitter 32 and the remaining light is reflected in the direction of a detector 39. A signal output from the detector 39 is input to a lock-in amplifier 40 as a reference signal. The laser light passing through the beam splitter 32 is refracted by a lens 33 and enters the sample 34.

The transmitted light/scattered light transmitted through the sample 34 is refracted by an objective lens 35. The transmitted light/scattered light enters a detector 41 through a dichroic mirror 36. The detector 41 is a photodiode (PD), for example, and receives light having the laser wavelength $\lambda$. Further, the dichroic mirror 36 reflects laser harmonics in the direction of a mirror 37. Accordingly, the light having the wavelength $\lambda/n$ (n is a natural number of 2 or more) serving as laser harmonics is reflected by the mirror 37 and enters a detector 42. The detector 42 is a photomultiplier (PMT) or a photodiode (PD), for example.

The reflection light/scattered light reflected by the sample 34 enters the beam splitter 32 through the lens 33 serving as an objective lens. Then, the reflection light/scattered light is reflected in the direction of a line filter 43 by the beam splitter 32. The line filter 43 is a filter that allows the light having the wavelength $\lambda$ to be transmitted, and blocks the light having the wavelength $\lambda/2$ or smaller. This enables separation of the signal light according to a wavelength difference.

The optical harmonics generated in the sample 34 are allowed to propagate only in directions that satisfy phase matching conditions. Thus, even when optical harmonics are generated, signals may be hardly detected depending on the angle between the crystal axis of the sample 34 and the incident polarization direction (Moreaux, JOSA B, 17 (2000) 1685). However, in the case of measuring a harmonic loss, the propagation direction of the optical harmonics has no effect on the measurement results. Since the polarization direction of the incident light contributes only to the generation efficiency of optical harmonics, an observation image that more faithfully reflects the shape of the sample is obtained in the microscope that measures the nonlinear optical loss. Thus, there is a large difference in mechanism for forming an image contrast between the case of detecting the nonlinear optical loss to create an image and the case of detecting the optical harmonics generated from a sample to create an image. Therefore, the detection of light having the fundamental wave enables measurement of the nonlinear optical loss.

A detector 38, the detector 39, the detector 41, and the detector 41 output detection signals according to the intensity of received light to the lock-in amplifier 40. These detection signals are demodulated by the lock-in amplifier 40. Each of the detector 41 and the detector 38 measures a laser fundamental wave. Specifically, the detector 41 detects scattered light/transmitted light having the same wavelength as that of the laser light, and the detector 38 detects scattered light/reflection light having the same wavelength as that of the laser light. The detector 42 receives the transmitted light/scattered light through the dichroic mirror 36 and the mirror 37, thereby detecting light having a wavelength n times (n is an integer of 2 or more) higher than the second harmonics, third harmonics, or the like of the laser light, that is, the laser wavelength $\lambda$. As a result, the generated harmonics are detected. The detector 39 measures a change in intensity of the laser light.

An upper limit of the order of each response to be detected is determined by a signal-to-noise ratio in measuring the intensity of the fundamental wave. In the measurement of the nonlinear optical loss, an extremely large number of photons can be used as signals because the laser light itself serves as signal light. Accordingly, the measurement can be made using the whole dynamic range of each detector, and the signal-to-noise ratio can be set to an extremely high level. It is also effective to use lock-in detection for the measurement of the nonlinear optical loss. A typical photodiode has a detection dynamic range of about 100 dB, which facilitates measurement of a higher-order nonlinear response.

For example, when super-resolution observation of a sample is performed using laser light having a wavelength of 400 nm, a higher-order nonlinear response is generated only in a central portion of a laser focal point. Therefore, a higher resolution can be obtained by increasing the demodulation frequency. The sample 34 is not limited to the nonlinear optical crystal, but crystal, semiconductor, and metal can also be used. Nanoparticles (having a diameter of about tens to hundreds of nm) of each material are used as the sample 34. The nonlinear optical loss generated on the surface of the sample 34 is measured and displayed as an image. Further, biomolecules (Campagnola, Nat. Biotechnol. 21 (2003) 1356, Debarre, Nat. Method, 3 (2006) 47) that efficiently generates optical harmonics, such as collagen, myosin, tubulin, and lipid, can also be used. That is, material that efficiently generates optical harmonics is preferably used as the sample 34.

In the case of applying laser light to metal, the reflection light can be efficiently saturated by utilizing plasmon resonance on the surface of the metal. That is, an electric field intensity is enhanced due to plasmon resonance, so that a nonlinear optical reaction is efficiently generated. In this case, metal particles or a metallic probe may be disposed in the vicinity of the sample. This allows the second harmonic generation, stimulated Raman scattering, and coherent anti-Stokes Raman scattering to be efficiently generated. In the case of detecting signal light while scanning the metal particles or metallic probe, a near-field optical microscope image can also be obtained with an improved spatial resolution.

Furthermore, the plasmon itself is saturated. In this case, the metal itself of the sample serves as a sample probe, like fluorescent dye in fluorescence observation. Accordingly, a harmonic loss occurs at a low laser intensity. This allows the reflection light to be efficiently saturated. In the case of using metal as a sample probe, metal particles are contained in the sample to be observed. Specifically, like in fluorescence labeling, metal particles are added to the sample. Since metal is not discolored, unlike fluorescence dye, the sample can be used for a long period of time without causing the problem of lifetime, even when the laser light intensity is increased. Incidence of a plasma resonance wavelength having a metal microstructure allows the saturation to be generated more efficiently.

EXAMPLE

Figure 15:
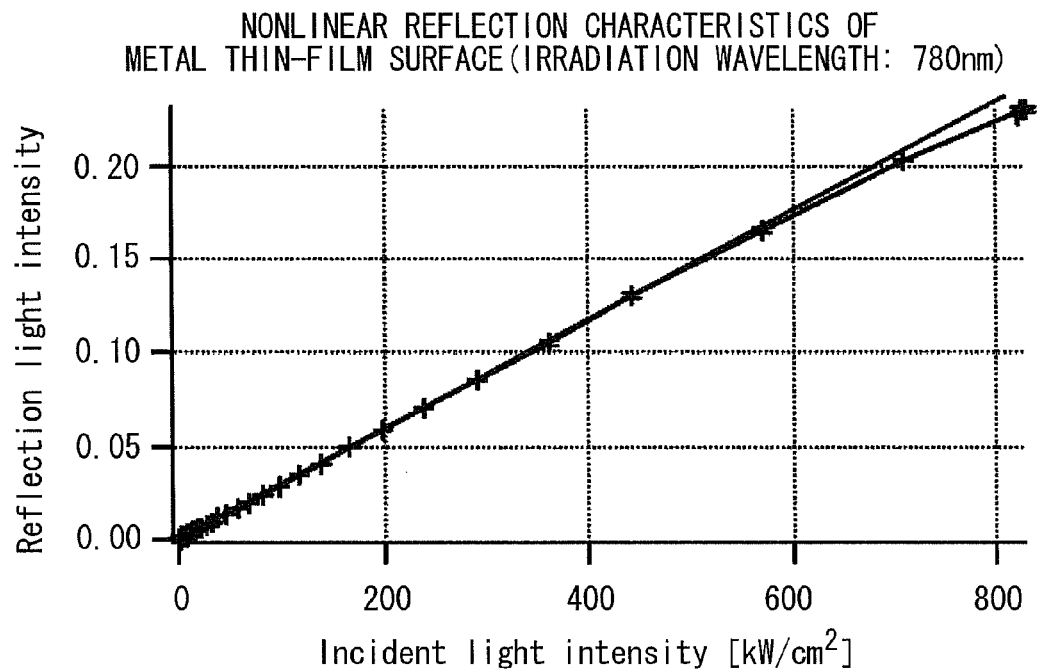
FIG. 15 is a graph showing nonlinear reflection characteristics of a gold thin-film surface.
Figure 16:
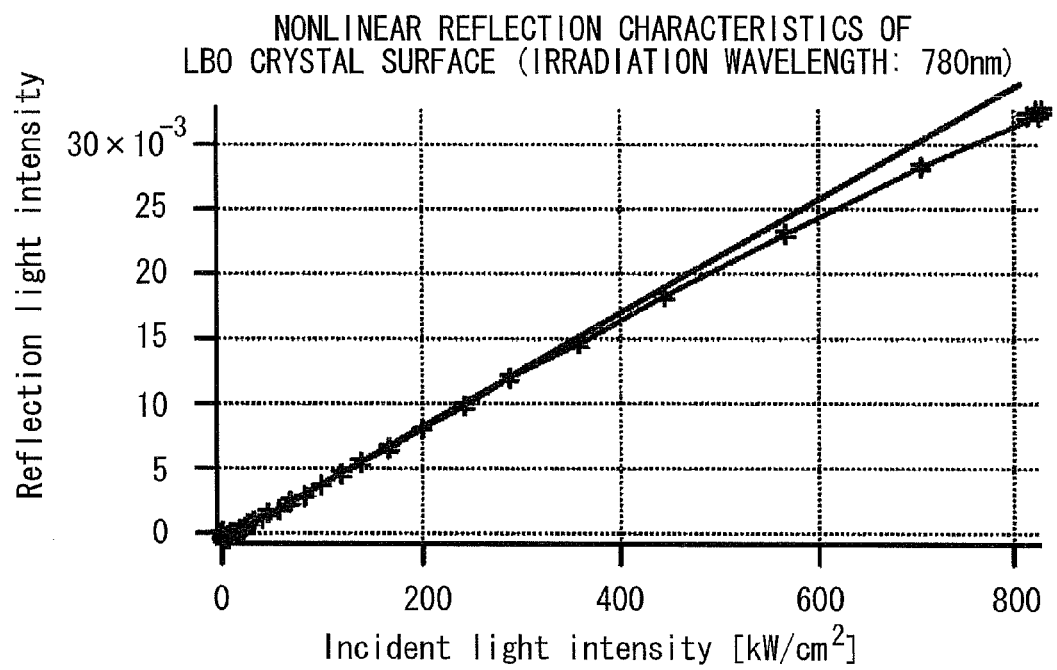
FIG. 16 is a graph showing nonlinear reflection characteristics of an LBO crystal surface.
Figure 17:
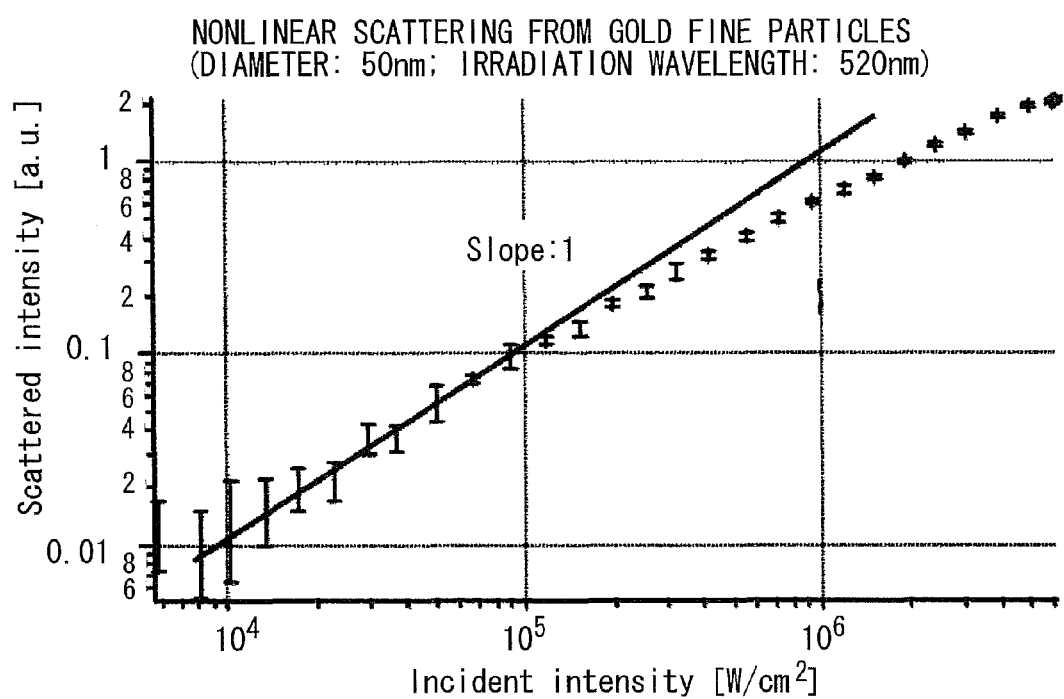
FIG. 17 is a graph showing nonlinear scattering characteristics from gold fine particles.
Figure 18:
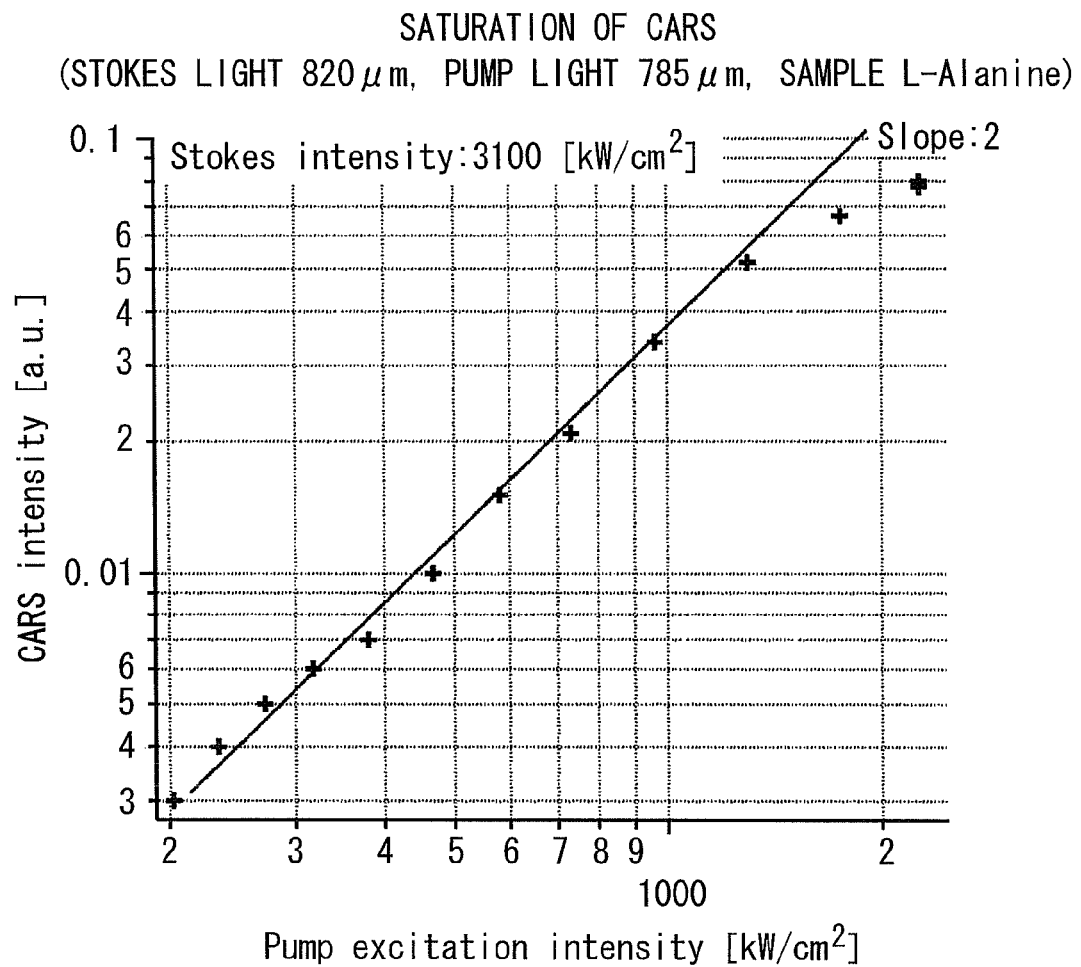
FIG. 18 is a graph showing saturation characteristics of CARS light from L-Alanine.

FIGS. 14 to 17 show the actual measurement results. FIG. 14 is a graph showing nonlinear reflection characteristics of a metal thin-film surface. In the measurement shown in FIG. 14, the laser wavelength was set to 780 nm. FIG. 15 is a graph showing nonlinear reflection characteristics of an LBO crystal surface. In the measurement shown in FIG. 15, the laser wavelength was set to 780 nm. FIG. 16 is a graph showing nonlinear scattering characteristics from gold fine particles. In the measurement shown in FIG. 16, the laser wavelength was set to 520 nm, and gold fine particles having a diameter of 50 nm were used. FIG. 17 is a graph showing saturation characteristics of CARS light from L-Alanine. In the measurement shown in FIG. 17, the wavelength of Stokes light was set to 820 nm and the wavelength of pump light was set to 785 nm. Further, the Stokes light intensity was set to 3100 kW/cm$^2$ to be kept constant, and the pump light was modulated.

As shown in FIGS. 14 to 17, in the region where the incident light intensity was low, the incident light intensity and the signal light intensity were proportional to each other. Meanwhile, when the incident light intensity was increased, the signal light intensity was saturated.

Other Embodiment

Though the laser light intensity is changed using a modulator in the above description, the laser light intensity may be changed by other methods. For example, as disclosed in Published Japanese Translation of PCT International Publication for Patent Application, No. 2006/061947, laser light is attenuated using a filter such as an ND filter. The use of a filter allows the laser light intensity to change stepwise. Further, when the laser light intensity becomes maximum, saturation of the signal light is generated. As a result, the same advantageous effects can be obtained. For example, the intensity of the laser light is changed such that signal light is applied to a sample with at least two intensities, i.e., a first intensity at which the signal light has the nonlinear region and a second intensity different from the first intensity. Then, saturation components of the signal light are calculated based on the intensity of the signal light at the first intensity and the intensity of the signal light at the second intensity.

Furthermore, various types of signal light may be detected simultaneously by multiple channels. Specifically, multiple detectors are provided and the detectors detect different types of signal light. In this case, the signal light may be separated according to a wavelength difference caused depending on the type of the signal light.

Though the observation is performed based on the saturation components of the signal light generated by the nonlinear optical effect in the above description, the observation may also be performed based on a nonlinear increase component of the signal light generated by the nonlinear optical effect. For example, in the case of using a saturable absorber as a sample or the like, a nonlinear increase occurs in the signal light. That is, the laser light and the signal light have no nonlinear relation, and the signal light rapidly increases according to an increase in the laser light intensity. In this case, the nonlinear increase component of the signal light can be extracted by demodulation with a higher-order modulation frequency. As a result, the same advantageous effects can be obtained. Though the laser light source that emits laser light is used in the above description, light sources that emit light other than laser light can also be used. Any type of light that is generated by a multi-photon transition process may be used as the signal light.

This application is based upon and claims the benefit of priority from Japanese patent application No. 2010-27838, filed on Feb. 10, 2010, the disclosure of which is incorporated herein in its entirety by reference.

INDUSTRIAL APPLICABILITY

The present invention is suitable for a microscope and an observation method that detect and observe various types of light, for example.

REFERENCE SIGNS LIST

10 LIGHT SOURCE
11 MODULATOR
12 DICHROIC MIRROR
13 SCANNER
14 LENS
15 LENS
16 OBJECTIVE LENS
17 SAMPLE
19 DICHROIC FILTER
20 LENS
21 PINHOLE
22 DETECTOR
23 LOCK-IN AMPLIFIER
24 PROCESSING APPARATUS
31 MODULATOR
32 BEAM SPLITTER
33 LENS
34 SAMPLE
35 OBJECTIVE LENS
36 DICHROIC MIRROR
37 MIRROR
38 DETECTOR
39 DETECTOR
30 LOCK-IN AMPLIFIER
41 DETECTOR
42 DETECTOR

The invention claimed is:

1. A microscope comprising:
at least one light source that emits light;
a lens that focuses light emitted from the light source and irradiates a sample with the light emitted from the at least one light source; and
at least one detector that detects signal light generated by a multi-photon transition process in the sample when the sample is irradiated with the light emitted from the at least one light source, wherein
the light emitted from the at least one light source is applied to the sample with an intensity changed to obtain a nonlinear region in which an intensity of the light emitted from the at least one light source and an intensity of the signal light have a nonlinear relation due to occurrence of saturation or nonlinear increase generated by a non-linear optical effect when the light emitted from the at least one light source has a maximum intensity,
the sample is irradiated with two light beams having different wavelengths,
the two light beams are modulated with different modulation frequencies, and
the detector detects the signal light according to the intensity of the light emitted from the at least one light source, and the signal light is demodulated with a frequency corresponding to one of a sum and a difference between the modulation frequencies of the two light beams to perform observation based on one of a saturation component and a nonlinear increase component of the signal light.

2. A microscope comprising:
at least one light source that emits light;
a lens that focuses light emitted from the light source and irradiates a sample with the light emitted from the at least one light source; and
at least one detector that detects signal light generated by a multi-photon transition process in the sample when the sample is irradiated with the light emitted from the at least one light source, wherein the light emitted from the at least one light source is applied to the sample with an intensity changed to obtain a nonlinear region in which an intensity of the light emitted from the at least one light source and an intensity of the signal light have a nonlinear relation due to occurrence of saturation or nonlinear increase generated by a non-linear optical effect when the light emitted from the at least one light source has a maximum intensity, the sample is irradiated with two light beams having different wavelengths, the two light beams are modulated with the same modulation frequencies and the same phase, the signal light from the sample is generated by an m-photon reaction (m is a natural number of 2 or more) of the two intensity-modulated light beams, and the detector detects the signal light according to the intensity of the light emitted from the at least one light source and extracts a (m+1) or higher-order harmonic component for the modulation frequency to perform observation based on one of a saturation component and a nonlinear increase component of the signal light.

3. The microscope according to claim 1, wherein
the detector detects, as the signal light, scattered light generated by a multi-photon transition, and generation of optical harmonics due to other optical effects including the nonlinear optical effect causes the signal light to be saturated.

4. The microscope according to claim 3, wherein
the detector detects at least one of hyper-Rayleigh scattering, Raman scattering, stimulated Raman scattering, coherent anti-Stokes Raman scattering, four wave mixing, stimulated emission, harmonics generation, difference frequency generation, and sum frequency generation, and signal light detected by the detector is separated from the light emitted from the at least one light source by using a wavelength difference from the light emitted from the light source.

5. A microscope comprising:
at least one light source that emits light;
a lens that focuses light emitted from the light source and irradiates a sample with the light emitted from the at least one light source; and
at least one detector that detects, as the signal light, at least one of reflection light, transmitted light, and scattered light generated with the same wavelength as that of the light from the light source upon application of the light emitted from the at least one light source to the sample, wherein
the light emitted from the at least one light source is applied to the sample with an intensity changed to obtain a nonlinear region in which an intensity of the light emitted from the at least one light source and an intensity of the signal light have a nonlinear relation due to occurrence of saturation generated by a non-linear optical effect of the signal light when the light emitted from the at least one light source has a maximum intensity, and
generation of optical harmonics due to other optical effects including a higher-order nonlinear optical effect causes the signal light serving as at least one of the reflection light, transmitted light, and scattered light to be saturated to perform observation based on a saturation component of the signal light.

6. The microscope according to claim 5, further comprising a modulator that performs intensity modulation such that the intensity of the light emitted from the at least one light source changes according to time, wherein the light emitted from the at least one light source is applied to the sample with an intensity where the signal light has the nonlinear region at a peak time of the light emitted from the at least one light source, the modulator performs intensity modulation and scans relative positions of the light emitted from the at least one light source and the sample such that the relative positions are changed, and the detector detects the signal light emitted from the sample, and a harmonic component for a modulation frequency in the modulator is extracted from the signal light detected by the detector and is observed.

7. The microscope according to claim 6, wherein
the signal light emitted from the sample is generated by an n-photon reaction (n is a natural number of 1 or more) of light, the intensity of the light emitted from the at least one light source being modulated by the modulator, and a (n+1) or higher-order harmonic component for the modulation frequency in the modulator is extracted and observed.

8. The microscope according to claim 5, wherein
intensity modulation is performed such that the intensity of the light emitted from the at least one light source changes according to time, the light source is a pulse light source, and
a repetition frequency of the pulse light source is higher than the modulation frequency for the intensity modulation.

9. The microscope according to claim 5, wherein
the intensity of the light emitted from the at least one light source is changed such that the signal light is applied to the sample with at least two intensities of a first intensity corresponding to the nonlinear region and a second intensity different from the first intensity, and one of a saturation component and a nonlinear increase component of the signal light is calculated based on the intensity of the signal light at the first intensity and the intensity of the signal at the second intensity.

10. The microscope according to claim 5, wherein the signal light separated according to a wavelength difference is detected by a plurality of the detectors.

11. An observation method that irradiates a sample with light emitted from at least one light source and observes the sample, the method comprising:
focusing two light beams having different wavelengths and irradiating the sample with the light beams to generate signal light by a multi-photon transition process in the sample;

modulating intensities of the two light beams with different modulation frequencies such that the signal light from the sample has a nonlinear region in which an intensity of the light emitted from the at least one light source and an intensity of the signal light have a nonlinear relation due to occurrence of one of saturation and nonlinear increase generated by a non-linear optical effect when the light emitted from the at least one light source has a maximum intensity;

detecting, by the detector, the signal light according to the intensity of the light emitted from the at least one light source and demodulating the signal light with a frequency corresponding to one of a sum and a difference between the modulation frequencies of the two light beams to perform observation based on one of a saturation component and a nonlinear increase component of the signal light.

12. An observation method that irradiates a sample with light emitted from at least one light source and observes the sample, the method comprising:
  focusing the light emitted from the at least one light source and irradiating the sample with the light emitted from the at least one light source to generate, as the signal light, at least one of reflection light, transmitted light, and scattered light having the same wavelength as that of the light from the light source;
  changing the intensity of the light emitted from the at least one light source such that the signal light from the sample has a nonlinear region in which an intensity of the light emitted from the at least one light source and an intensity of the signal light have a nonlinear relation due to saturation of the signal light generated by a non-linear optical effect when the light emitted from the at least one light source has a maximum intensity; and
  generating optical harmonics due to other optical effects including a higher-order nonlinear optical effect to cause the signal light serving as at least one of the reflection light, transmitted light, and scattered light to be saturated to perform observation based on a saturation component of the signal light.

13. The observation method according to claim 11, wherein the sample is irradiated with the light emitted from the at least one light source in a state where a metallic probe is placed near the sample with the light irradiation or in a state where metal particles are added to the sample.

14. The observation method according to claim 13, wherein the signal light is detected by scanning the metallic probe placed near the sample with the light irradiation and irradiating the sample with the light emitted from the at least one light source.

15. The microscope according to claim 2, wherein
  the detector detects, as the signal light, scattered light generated by a multi-photon transition, and
  generation of optical harmonics due to other optical effects including the nonlinear optical effect causes the signal light to be saturated.

16. The microscope according to claim 1, wherein
  intensity modulation is performed such that the intensity of the light emitted from the at least one light source changes according to time,
  the light source is a pulse light source, and
  a repetition frequency of the pulse light source is higher than the modulation frequency for the intensity modulation.

17. The microscope according to claim 2, wherein
  intensity modulation is performed such that the intensity of the light emitted from the at least one light source changes according to time,
  the light source is a pulse light source, and
  a repetition frequency of the pulse light source is higher than the modulation frequency for the intensity modulation.

18. The microscope according to claim 1, wherein the signal light separated according to a wavelength difference is detected by a plurality of the detectors.

19. The microscope according to claim 2, wherein the signal light separated according to a wavelength difference is detected by a plurality of the detectors.

20. The observation method according to claim 12, wherein the sample is irradiated with the light emitted from the at least one light source in a state where a metallic probe is placed near the sample with the light irradiation or in a state where metal particles are added to the sample.

* * * * *